(12) United States Patent
Takayama et al.

(10) Patent No.: US 8,426,516 B2
(45) Date of Patent: Apr. 23, 2013

(54) POLYMER COMPOUND HAVING AROYLBIPHENYLENE SKELETON AND THERMOCURABLE FILM FORMING POLYMER COMPOSITION

(75) Inventors: Yuki Takayama, Funabashi (JP); Tadashi Hatanaka, Funabashi (JP); Kei Yasui, Funabashi (JP); Daigo Saito, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 266 days.

(21) Appl. No.: 12/920,854

(22) PCT Filed: Mar. 9, 2009

(86) PCT No.: PCT/JP2009/054457
§ 371 (c)(1),
(2), (4) Date: Dec. 7, 2010

(87) PCT Pub. No.: WO2009/110634
PCT Pub. Date: Sep. 11, 2009

(65) Prior Publication Data
US 2011/0118408 A1 May 19, 2011

(30) Foreign Application Priority Data

Mar. 7, 2008 (JP) .................. 2008-058349
Apr. 11, 2008 (JP) .................. 2008-103765

(51) Int. Cl.
C08L 61/02 (2006.01)
C07C 49/00 (2006.01)

(52) U.S. Cl.
USPC ............ 524/592; 525/471; 528/220; 568/327

(58) Field of Classification Search .................. 524/592; 525/471; 528/220; 568/327
See application file for complete search history.

(56) References Cited

U.S. PATENT DOCUMENTS

| | | | |
|---|---|---|---|
| 5,886,130 | A | 3/1999 | Trimmer et al. |
| 2004/0077824 | A1 | 4/2004 | O'Dell et al. |
| 2007/0034832 | A1 | 2/2007 | O'Dell et al. |

FOREIGN PATENT DOCUMENTS

| | | |
|---|---|---|
| JP | 07041555 A * | 2/1995 |
| JP | A-09-059355 | 3/1997 |
| JP | A-2004-532291 | 10/2004 |
| JP | A-2005-060626 | 3/2005 |
| JP | A-2005-232211 | 9/2005 |
| JP | A-2006-290771 | 10/2006 |
| JP | A-2007-161859 | 6/2007 |

* cited by examiner

*Primary Examiner* — Vickey Nerangis
(74) *Attorney, Agent, or Firm* — Oliff & Berridge, PLC

(57) ABSTRACT

There is provided a polymer compound having excellent transparency and excellent heat resistance, a high refractive index, an excellent solubility in various solvents, and a low viscosity and excellent handling properties when the polymer compound is dissolved in a solvent; and a production method of the polymer compound; and a polymer composition containing the polymer compound. And there is also included an aroylbiphenyl compound of Formula (1):

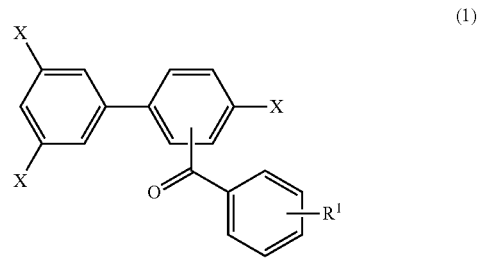

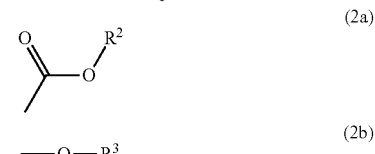

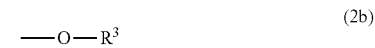

[in Formula (1), X is a halogen atom, and $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group]; a polymer compound obtained by using the aroylbiphenyl compound; and a thermocurable film forming polymer composition comprising: as a component (A), the polymer compound, and as a component (B), a crosslinkable compound.

17 Claims, 8 Drawing Sheets

(¹H-NMR OF COMPOUND [5] OBTAINED IN EXAMPLE 2)

(¹H-NMR OF COMPOUND [12] OBTAINED IN EXAMPLE 4)

(¹H-NMR OF COMPOUND [13] OBTAINED IN EXAMPLE 5)

(¹H-NMR OF COMPOUND [17] OBTAINED IN EXAMPLE 7)

($^1$H-NMR OF COMPOUND [21] OBTAINED IN EXAMPLE 9)

(¹H-NMR OF COMPOUND OBTAINED IN COMPARATIVE EXAMPLE 1)

UV-Vis OF EXAMPLE 2 (POST-BAKE: 300°C)

(EXAMPLE 2)

(EXAMPLE 5)

POLYMER COMPOUND HAVING AROYLBIPHENYLENE SKELETON AND THERMOCURABLE FILM FORMING POLYMER COMPOSITION

TECHNICAL FIELD

The present invention relates to an aroylbiphenyl compound, a polymer compound having a biphenylene skeleton, a production method of these compounds, a solution and a coating film each containing the polymer compound, a thermocurable polymer composition containing the polymer compound having a biphenylene skeleton and a crosslinkable compound, and a cured film of the thermocurable polymer composition.

BACKGROUND ART

Hitherto, various attempts to multifunctionalize a polymer compound have been performed. For example, as a method for making a polymer compound having a high refractive index, the introduction of an aromatic ring, a halogen atom, or a sulfur atom has been performed. Particularly, an episulfide polymer compound and a thiourethane polymer compound in which a sulfur atom is introduced have been in practical use as a lens having a high refractive index for an eyeglass.

A number of attempts to impart heat resistance have also been performed and it is well-known that, for these attempts, a polymer compound in which an aromatic ring is introduced is applied. For example, there is disclosed a polyarylene copolymer having a substituted arylene repeating unit in the backbone thereof (see, for example, Patent Document 1). The polymer compound is expected to be applied mainly to a heat resistant plastic. There is also disclosed a polyphenylene compound obtained by a Diels-Alder reaction between a tetraethynyl compound and a bisdiene compound having a regular tetrahedron structure (see, for example, Patent Document 2).

Patent Document 1: U.S. Pat. No. 5,886,130 specification
Patent Document 2: Japanese Patent Application Publication No. JP-A-2005-232211

DISCLOSURE OF THE INVENTION

Problem to be Solved by the Invention

By the way, recently, in a liquid crystal display which is a representative optical switching element and an organic EL (electroluminescent) display which is a self-emission element, the utilization of light with high efficiency has become an essential technology for further compatibilizing the lowering of power consumption with the enhancement of luminance. Also in an imaging element and an LED element which are optical semiconductors, for the same reason, it has become an essential technical task to efficiently utilize light. In such a photoelectronic material field, as one of the methods for overcoming the above problems, there has been required a polymer compound having a high refractive index and combining transparency and heat resistance.

However, the polymer compound in which an aromatic ring is introduced has generally an unsatisfactory solubility in a solvent or even when the polymer compound can be dissolved in a solvent, the polymer compound can be dissolved only in a limited solvent and the resultant solution of the polymer compound has an extremely high viscosity, etc., so that the polymer compound has less-than-satisfactory practicality. Even when the polymer compound has a high solubility in a solvent, the resultant solution is colored or has low transparency, so that the polymer compound is difficult to compatibilize a high refractive index with high transparency.

The present invention has been achieved based on the above circumstances, and it is an object of the present invention to provide: a polymer compound having such characteristics as excellent transparency and heat resistance, a high refractive index, excellent solubility in various solvents, and a low viscosity and excellent handling properties when the polymer compound is made into a solution; and a production method of the polymer compound.

It is another object of the present invention to provide a solution containing the polymer compound and a coating film containing the polymer compound. It is yet another object of the present invention to provide a compound that is to be a raw material for the polymer compound and a production method of the compound.

It is yet another object of the present invention to provide a polymer composition which contains the polymer compound and a crosslinkable compound, which has such characteristics as an excellent solubility in various solvents and a low viscosity and excellent handling properties when the polymer composition is made into a solution, and from which a film can be obtained that has excellent transparency and heat resistance, a high refractive index, and solvent resistance.

Means for Solving the Problem

As a result of assiduous research intended to overcome these disadvantages, the inventors of the present invention found that a polymer compound constructed as having a biphenylene skeleton has excellent transparency and excellent heat resistance, has a high refractive index, has an excellent solubility in various solvents, and has a low viscosity and excellent handling properties when the polymer compound is made into a solution, and completed the present invention.

Further, the inventors of the present invention found that by adopting a constitution of a composition containing the polymer compound having a biphenylene skeleton and a crosslinkable compound, the composition has an excellent solubility in various solvents and has a low viscosity and excellent handling properties when the composition is made into a solution, and when the composition is cured, there can be obtained a cured film having excellent transparency and excellent heat resistance, having a high refractive index, and having excellent solvent resistance, and completed the present invention.

Specifically, the present invention provides, according to a first aspect, a polymer compound containing a structure unit of Formula (3):

(3)

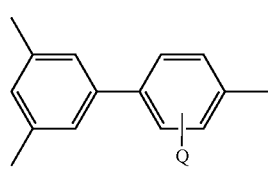

(4)

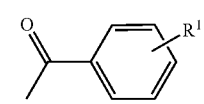

(2a)

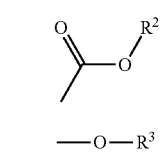

(2b)

—O—R³

[in Formula (3), Q is a hydrogen atom or a group of Formula (4); in Formula (4), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group].

According to a second aspect, in the polymer compound according to the first aspect, in Formula (4), $R^1$ is a group of Formula (2a).

According to a third aspect, in the polymer compound according to the first aspect, in Formula (4), $R^1$ is a group of Formula (2b).

According to a fourth aspect, a solution contains the polymer compound as described in any one of the first aspect to the third aspect.

According to a fifth aspect, a coating film contains the polymer compound as described in any one of the first aspect to the third aspect.

According to a sixth aspect, an aroylbiphenyl compound of Formula (1):

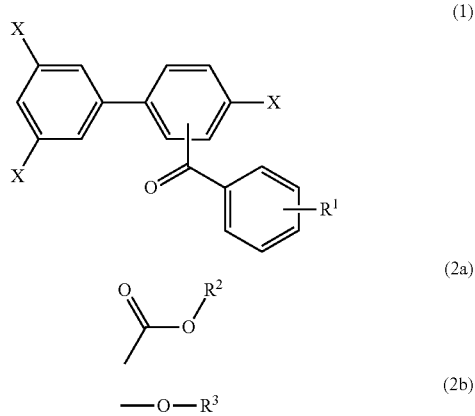

[in Formula (1), X is a halogen atom and $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group].

According to a seventh aspect, a thermocurable film forming polymer composition contains, as a component (A), a polymer compound containing a structure unit of Formula (19):

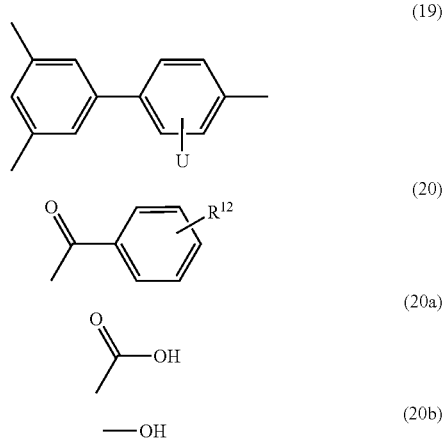

[in Formula (19), U is a group of Formula (20); and in Formula (20), $R^{12}$ is a group of Formula (20a) or Formula (20b)]; and as a component (B), a crosslinkable compound.

According to an eighth aspect, in the thermocurable film forming polymer composition according to the seventh aspect, in Formula (20), $R^{12}$ is a group of Formula (20a).

According to a ninth aspect, in the thermocurable film forming polymer composition according to the seventh aspect or the eighth aspect, the component (A) is a polymer compound consisting of a structure unit of Formula (19).

According to a tenth aspect, in the thermocurable film forming polymer composition according to any one of the seventh aspect to the ninth aspect, the component (B) is a crosslinkable compound having an epoxy group or a crosslinkable compound having an oxetanyl group.

According to an eleventh aspect, in the thermocurable film forming polymer composition according to any one of the seventh aspect to the tenth aspect, the component (A) and the component (B) are in a solution state of being dissolved in an organic solvent.

According to a twelfth aspect, a cured film is obtained using the thermocurable film forming polymer composition as described in any one of the seventh aspect to the eleventh aspect.

According to a thirteenth aspect, a solid imaging element includes the cured film as described in the twelfth aspect.

According to a fourteenth aspect, an LED element includes the cured film as described in the twelfth aspect.

According to a fifteenth aspect, a production method of a polymer compound includes polymerizing a compound of Formula (18):

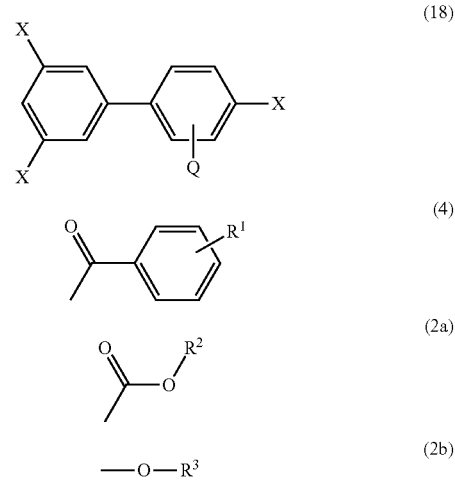

[where X is a halogen atom and Q is a hydrogen atom or a group of Formula (4); in Formula (4), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group]

in the presence of at least one of a nickel complex and a palladium complex.

According to a sixteenth aspect, a production method of the aroylbiphenyl compound as described in the sixth aspect, is characterized by including reacting a compound of Formula (5) with a compound of Formula (6):

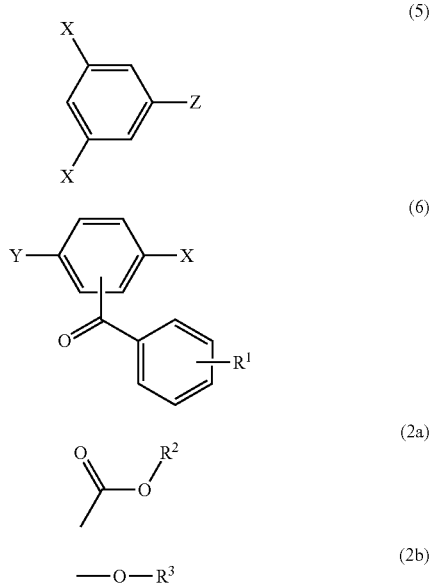

[in Formula (5) and Formula (6), X is a halogen atom and Z and Y are a group selected from a group A below or a group B below, when Z is a group selected from the group A, Y is a group selected from the group B, and when Z is a group selected from the group B, Y is a group selected from the group A; in Formula (6), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group], Group A: $MgR^4$, Li, $Al(R^4)_2$, $ZnR^4$, $Sn(R^5)_3$, $B(OR^6)_2$, $Si(R^5)_3$ (in these formulae, $R^4$ is a halogen atom or a $C_{1-6}$ alkoxy group, $R^5$ is a halogen atom, a $C_{1-6}$ alkyl group, or a $C_{1-6}$ alkoxy group, $R^6$ is a hydrogen atom or a $C_{1-6}$ alkyl group), Group B: a halogen atom, $R^7SO_3$ ($R^7$ is a $C_{1-10}$ alkyl group, a $C_{1-10}$ alkyl group substituted with a fluorine atom, or a benzene ring (which may be substituted with an alkyl group)) in the presence of a transition metal catalyst.

According to a seventeenth aspect, a production method of the aroylbiphenyl compound as described in the sixth aspect, is characterized by including reacting a compound of Formula (7) with an aromatic metal compound of Formula (8):

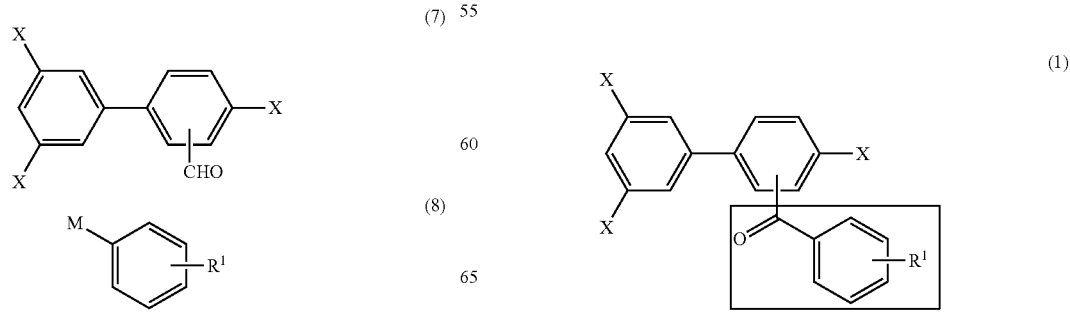

[in Formula (7), X is a halogen atom; in Formula (8), M is $MgR^4$, Li, $Al(R^4)_2$, $ZnR^4$, $Ti(R^4)_3$, or $Zr(R^4)_3$ (in these formulae, $R^4$ is a halogen atom or a $C_{1-6}$ alkoxy group), and $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group], and oxidizing a hydroxy group Effects of the Invention By the present invention, there is provided a polymer compound having excellent transparency and heat resistance, a high refractive index, excellent solubility in various solvents, and a low viscosity, and consequently having excellent handling properties when the polymer compound is dissolved in a solvent, although the polymer compound has a high molecular weight.

Therefore, the polymer compound and a solution and a coating film each containing the compound according to the present invention can obtain such an effect as being suitably used in the photoelectronic material field by the virtue of excellent properties and high handling properties thereof.

Further, by the production method of the present invention, the polymer compound can be easily produced and, moreover, the production method has such an advantage as easily producing an aroylbiphenyl compound that is a raw material for the polymer compound.

By the present invention, there is provided a thermocurable film forming polymer composition having an excellent solubility in various solvents and having a low viscosity and consequently having excellent handling properties when the polymer composition is dissolved in a solvent made into a solution state, although the polymer composition contains a compound having a high molecular weight.

Then, by thermocuring the composition, there can be obtained a cured film having excellent transparency and excellent heat resistance, having a high refractive index, and having excellent solvent resistance.

Therefore, the thermocurable film forming polymer composition of the present invention and a cured film obtained from the compound can obtain such an effect as being suitably used in the photoelectronic material field by the virtue of excellent properties and high handling properties thereof.

BEST MODES FOR CARRYING OUT THE INVENTION

[Aroylbiphenyl Compound]

The aroylbiphenyl compound of the present invention is a novel biphenyl compound of Formula (1):

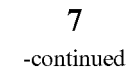

(2a)

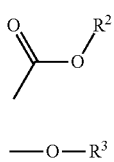

(2b)

In Formula (1), X is a halogen atom and $R^1$ is a hydrogen atom or a group of Formula (2a) or Formula (2b). In Formula (2a) and Formula (2b), $R^2$ and $R^3$ are independently a hydrogen atom or a $C_{1-6}$ alkyl group.

The position of a ketone moiety (the moiety enclosed with a dotted line) in Formula (1) may be any one of the 2-position and the 3-position.

The substituted position of $R^1$ in Formula (1) may be any one of the ortho position, the meta position, and the para position.

In Formula (1), X is a halogen atom, that is, is selected from F, Cl, Br, and I. However, in consideration of high polymerizability required when the present biphenyl compound is regarded as a monomer, X is preferably selected from Cl, Br, and I.

Further, when taking into account the easiness of producing the compound of Formula (1) itself, X is more preferably Cl or Br.

In Formula (1), $R^1$ is selected from a hydrogen atom and a group of Formula (2a) or Formula (2b). However, in consideration of the solubility in a solvent and the film formation property of a polymer obtained by polymerizing the present compound, $R^1$ is preferably a group of Formula (2a) or Formula (2b).

Both of $R^2$ in Formula (2a) and $R^3$ in Formula (2b) are a hydrogen atom or a $C_{1-6}$ alkyl group and the alkyl group may be branched. In consideration of reaction conditions during the polymerization, both of $R^2$ and $R^3$ are preferably an alkyl group.

[Production Method [1] of Aroylbiphenyl Compound]

The aroylbiphenyl compound of Formula (1) of the present invention is generally produced according to the following scheme.

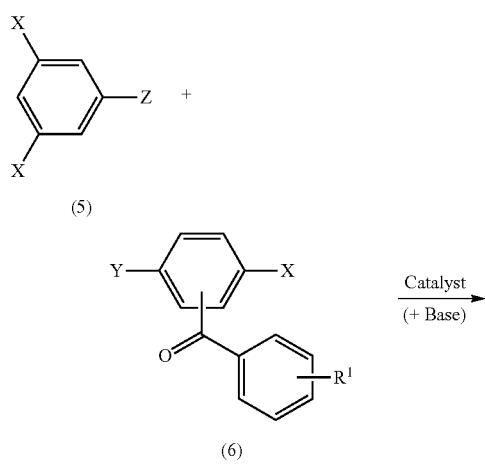

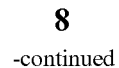

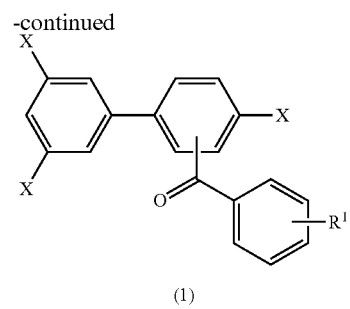

(1)

In other words, a compound of Formula (5) and a compound of Formula (6) are subjected to a coupling reaction in the presence of a transition metal catalyst such as a palladium complex, a copper complex, and a nickel complex and, if necessary, a base in a solvent to obtain the compound of Formula (1).

In the scheme, $R^1$ and X are the same as those defined above.

In Formula (6), Y is selected from a halogen atom and $R^7SO_3$ (where $R^7$ is a $C_{1-10}$ alkyl group, a $C_{1-10}$ alkyl group substituted with a fluorine atom, or a benzene ring (which may be substituted with an alkyl group)).

In Formula (5), Z is selected from $MgR^4$, Li, $Al(R^4)_2$, $ZnR^4$, $Sn(R^5)_3$, $B(OR^6)_2$, and $Si(R^5)_3$, and is preferably $B(OR^6)_2$ or $Si(R^5)_3$ (in these formulae, $R^4$ is a halogen atom or a $C_{1-6}$ alkoxy group, $R^5$ is a halogen atom, a $C_{1-6}$ alkyl group, or a $C_{1-6}$ alkoxy group, and $R^6$ is a hydrogen atom or a $C_{1-6}$ alkyl group).

The definition of Z and the definition of Y may be exchanged with each other.

The catalyst used during the above synthesis reaction is not particularly limited so long as the catalyst is a transition metal catalyst. However, among the above catalysts, a palladium complex is preferred to be used. As the palladium complex, those complexes having various structures may be used. However, particularly preferred is a low-valence palladium complex having a ligand of a tertiary phosphine or a tertiary phosphite. There may also be used, as the catalyst, an appropriate precursor capable of being easily converted into a zero-valence complex in the reaction system.

A palladium complex containing no tertiary phosphine or no tertiary phosphite as a ligand may be mixed with a tertiary phosphine or a tertiary phosphite in the reaction system to generate a low-valence complex having a tertiary phosphine or a tertiary phosphite as a ligand.

Further, a palladium catalyst containing no tertiary phosphine or no tertiary phosphite and/or a palladium catalyst containing a tertiary phosphine or a tertiary phosphite may be used in combination with the ligand (a tertiary phosphine or a tertiary phosphite).

Examples of the palladium catalyst containing no tertiary phosphine or no tertiary phosphite include bis(dibenzylideneacetone) palladium, tris(dibenzylideneacetone) dipalladium, palladium acetate, palladium chloride, and palladium on activated carbon.

Examples of the palladium complex already containing a tertiary phosphine or a tertiary phosphite as a ligand include dimethylbis(triphenylphosphine) palladium, dimethylbis(diphenylmethylphosphine) palladium, (ethylene)bis(triphenylphosphine) palladium, tetrakis(triphenylphosphine) palladium, and bis(triphenylphosphine) palladium dichloride.

Examples of the tertiary phosphine or the tertiary phosphite applicable as a ligand include triphenylphosphine, 1,2-bis(diphenylphosphino)ethane, 1,3-bis(diphenylphosphino)

propane, 1,4-bis(diphenylphosphino)butane, tri(tert-butyl)phosphine, 1,1'-bis(diphenylphosphino)ferrocene, 1,2'-bis(diphenylphosphino)-1,1'-binaphthalenetrimethylphosphite, triethylphosphite, and triphenylphosphite.

There may also be used a palladium complex prepared by mixing two or more types of these ligands to form a complex.

The used amount of the palladium complex is satisfactorily 20 mol % or less, usually 10 mol % or less, based on the amount of the raw material.

In the above synthesis reaction, if necessary, a base may be used as it is or in the form of an aqueous solution thereof according to reaction conditions. Examples of the appropriate base include: inorganic bases such as sodium hydroxide, potassium hydroxide, lithium hydroxide, sodium carbonate, sodium hydrogen carbonate, potassium hydrogen carbonate, potassium phosphate, potassium carbonate, and cesium carbonate; and organic bases, for example aliphatic amines such as triethylamine and diisopropylethylamine, and aromatic amines such as pyridine, quinoline, and imidazole.

The solvent used in the synthesis reaction is not particularly limited so long as the solvent is stable and inactive under the reaction conditions and does not inhibit the synthesis reaction. Specific examples of the solvent include water, alcohols, aprotic polar organic solvents (such as DMF (N,N-dimethylformamide), DMSO (dimethylsulfoxide), DMAc (N,N-dimethylacetamide), and NMP (N-methyl-2-pyrrolidone)), ethers (such as Et$_2$O (diethyl ether), i-Pr$_2$O (diisopropyl ether), TBME (tert-butyl methyl ether), CPME (cyclopentyl methyl ether), THF (tetrahydrofuran), and dioxane), aliphatic hydrocarbons (such as pentane, hexane, and petroleum ether), aromatic hydrocarbons (such as benzene, toluene, xylene, mesitylene, chlorobenzene, dichlorobenzene, nitrobenzene, and tetralin), halogenated hydrocarbons (such as chloroform, dichloromethane, carbon tetrachloride, and 1,2-dichloroethane), ketones (such as acetone and methyl ethyl ketone), lower aliphatic acid esters (such as methyl acetate, ethyl acetate, butyl acetate, and methyl propionate), and nitriles (such as acetonitrile, propionitrile, and butyronitrile).

The reaction temperature for the synthesis reaction may be in a range of −100° C. to the boiling point of a used solvent and is preferably in a range of −50 to 150° C.

The reaction time is preferably 0.1 to 1,000 hours.

Finally, a crude product obtained by the synthesis reaction is purified using distillation, silica gel column chromatography, recrystallization, or the like to obtain an aroylbiphenyl compound of Formula (1).

[Production Method [2] of Aroylbiphenyl Compound]

As another production method of the aroylbiphenyl compound of the present invention, there can be mentioned the following scheme.

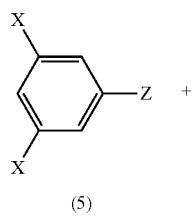

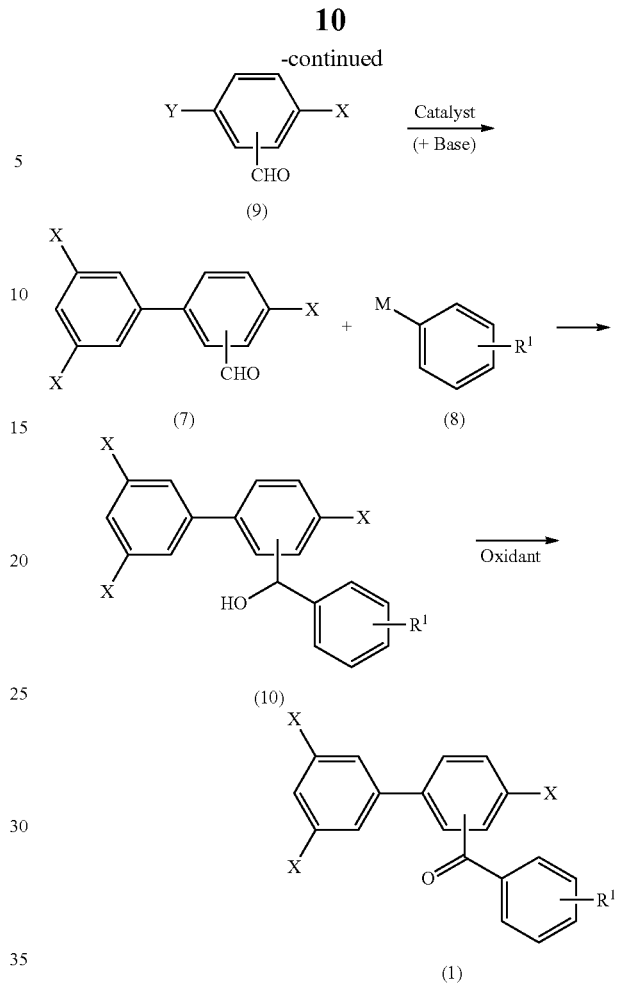

In other words, a compound of Formula (5) and a compound of Formula (9) are subjected to a coupling reaction in the presence of a transition metal catalyst such as a palladium complex, a copper complex, and a nickel complex and, if necessary, a base in a solvent to obtain a compound (intermediate 1) of Formula (7). Thereafter, the intermediate 1 is reacted with an aromatic metal compound of Formula (8) having R$^1$ to convert the intermediate 1 into an alcohol compound of Formula (10) and, finally, a hydroxy group in Formula (10) is oxidized to obtain the compound of Formula (1).

In the above formula, R$^1$, X, Y, and Z are the same as those defined above.

In Formula (8), M is a functional group addition reactable to an aldehyde group in Formula (7) and is preferably selected from MgR$^4$, Li, Al(R$^4$)$_2$, ZnR$^4$, Ti(R$^4$)$_3$, and Zr(R$^4$)$_3$ (in these formulae, R$^4$ is a halogen atom or a C$_{1-6}$ alkoxy group).

The oxidant used for the oxidation of the compound of Formula (10) is satisfactorily an oxidant that does not oxidize a substituent X on benzene and examples thereof include chromium-based oxidants, DMSO-based oxidants, manganese-based oxidants, and TEMPO (tetramethylpiperidine oxy radical).

Preferred examples of the transition metal catalyst and of the base used in the scheme individually include the compounds exemplified in the production method [1] of the aroylbiphenyl compound.

As a series of preferred reaction conditions (reaction temperature, reaction time, and solvent) and preferred purification methods in the scheme, the reaction conditions and the purification methods exemplified in the production method [1] can be used.

[Production Method of the Compound of Formula (6) and the Compound of Formula (9) that are Raw Material Compounds for the Aroylbiphenyl Compound]

In the production method [1] or [2] of the aroylbiphenyl compound, as the compound of Formula (6) or the compound of Formula (9) used as the raw material compound, there may be used commercially available products (in Formulae, Y is a halogen atom).

When, in the compound of Formula (6) or the compound of Formula (9), Y is not a halogen atom, that is, Y is a $R^7SO_3$ group (where $R^7$ is a $C_{1-10}$ alkyl group, a $C_{1-10}$ alkyl group substituted with a fluorine atom, or a benzene ring (which may be substituted with an alkyl group)), the compound of Formula (6) or the compound of Formula (9) can be obtained according to the following scheme by reacting a phenol compound of Formula (11) having a substituent P with a corresponding sulfonyl chloride or a corresponding sulfonic anhydride in the presence of a base in a solvent.

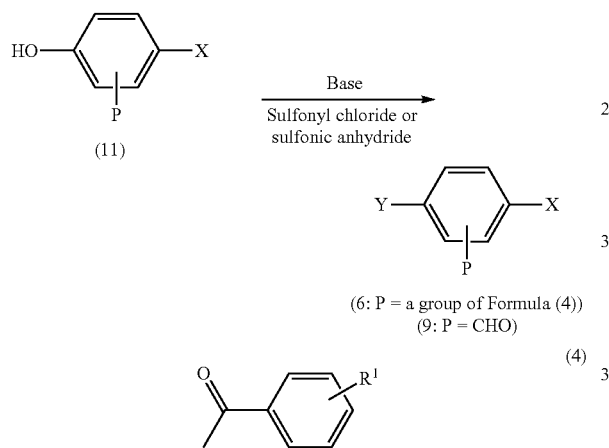

In the scheme, X, Y, and $R^1$ are the same as those defined above.

Examples of the sulfonyl chloride used in the synthesis reaction include methanesulfonyl chloride and toluenesulfonyl chloride. Examples of the sulfonic anhydride include methanesulfonic anhydride, toluenesulfonic anhydride, and trifluoromethanesulfonic anhydride.

Examples of the base used in the synthesis reaction include, besides sodium hydride, potassium hydride, butyllithium, and tert-butoxy potassium, the inorganic bases and the organic bases exemplified in the production method [1] of the aroylbiphenyl compound.

As the solvent used in the synthesis reaction, various solvents exemplified in the production method [1] of the aroylbiphenyl compound can be suitably used.

The reaction temperature for the synthesis reaction may be in a range of −100° C. to the boiling point of a used solvent and is desirably in a range of −50 to 150° C.

The reaction time is preferably 0.1 to 1,000 hours.

Finally, a crude product obtained by the synthesis reaction is purified using distillation, silica gel column chromatography, recrystallization, or the like to obtain a compound of Formula (6) or Formula (9).

[Another Production Method [3] of Aroylbiphenyl Compound]

The aroylbiphenyl compound of Formula (1) of the present invention can be produced, besides the production methods [1] and [2], according to the following scheme.

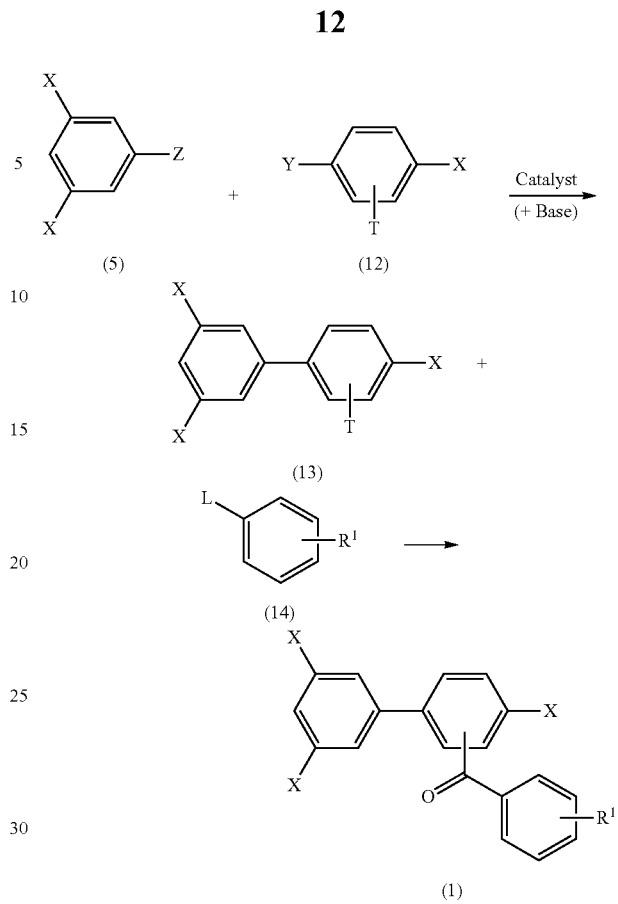

In other words, a compound of Formula (5) and a compound of Formula (12) having a functional group T are subjected to a coupling reaction in the presence of a transition metal catalyst such as a palladium complex, a copper complex, and a nickel complex and, if necessary, a base in a solvent to obtain a compound (intermediate 2) of Formula (13). Thereafter, the intermediate 2 is reacted with an aromatic compound of Formula (14) having $R^1$ to obtain the aroylbiphenyl compound of Formula (1).

In the scheme, X, Y, Z, and $R^1$ are the same as those defined above.

In Formula (12), the substituent T is selected from a cyano group, a carboxy group, and an alkoxycarbonyl group. Therefore, the present production method [3] can omit an oxidation process required for the production method [2].

In Formula (14), L is a functional group addition reactable to a functional group T (a cyano group, a carboxy group, or an alkoxycarbonyl group) and is preferably selected from $MgR^4$ ($R^4$ is a halogen atom or a $C_{1-6}$ alkoxy group) and Li.

Preferred examples of the transition metal catalyst and of the base used in the scheme individually include the compounds exemplified in the production method [1] of the aroylbiphenyl compound.

As a series of preferred reaction conditions (reaction temperature, reaction time, and solvent) and preferred purification methods in the scheme, the reaction conditions and the purification methods exemplified in the production method [1] can be used.

[Another Production Method [4] of Aroylbiphenyl Compound]

The aroylbiphenyl compound of Formula (1) of the present invention can be produced, besides the production methods [1] to [3], according to the following scheme.

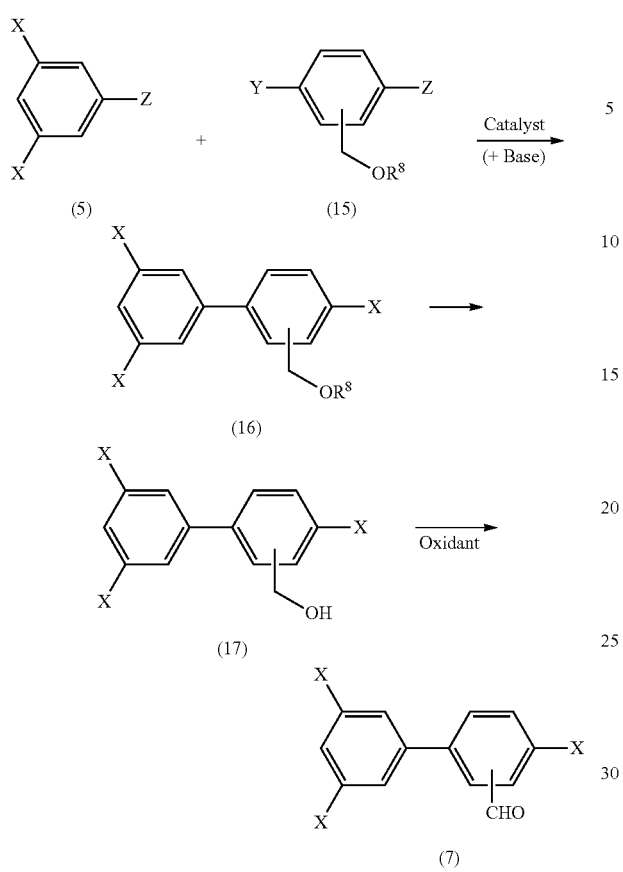

In other words, a compound of Formula (5) and a benzyl alcohol compound of Formula (15) are subjected to a coupling reaction in the presence of a transition metal catalyst such as a palladium complex, a copper complex, and a nickel complex and, if necessary, a base in a solvent to obtain a compound (intermediate 3) of Formula (16). Thereafter, the deprotection of the intermediate 3 is performed to convert the intermediate 3 into an alcohol compound of Formula (17) and then a hydroxy group is oxidized to obtain an aldehyde compound of Formula (7).

The thus obtained compound of Formula (7) can be converted into the aroylbiphenyl compound of Formula (1) using the method described in the production method [2].

In the scheme, X, Y, and Z are the same as those defined above.

In the scheme, $R^8$ is not particularly limited so long as $R^8$ is a substituent applicable as a protection group for a hydroxy group. However, $R^8$ is preferably a group selected from a $C_{1-10}$ alkyl group, a triphenylmethyl group, a $C_{1-10}$ acyl group, a $C_{1-10}$ alkoxycarbonyl group, a tetrahydropyran group, a methoxymethyl group, a 1-ethoxyethyl group, and $Si(R^{10})_3$ ($R^{10}$ is a $C_{1-10}$ alkyl group or a phenyl group).

Preferred examples of the transition metal catalyst and of the base used in the scheme individually include the compounds exemplified in the production method [1] of the aroylbiphenyl compound.

The deprotection can be performed using a base, an acid, or a fluoride. Examples of the base used for the deprotection include sodium hydroxide, potassium hydroxide, lithium hydroxide, sodium carbonate, potassium carbonate, sodium hydrogen carbonate, potassium hydrogen carbonate, and potassium phosphate. Examples of the acid include: inorganic acids such as hydrochloric acid, sulfuric acid, and phosphoric acid; and organic acids such as formic acid and toluenesulfonic acid. Examples of the fluoride include sodium fluoride, potassium fluoride, cesium fluoride, and $(R^{11})_4NF$ (where $R^{11}$ is a $C_{1-10}$ alkyl group).

Further, the oxidant used for the oxidation of the compound of Formula (17) is not particularly limited so long as the oxidant can oxidize a hydroxy group to an aldehyde group. Preferred examples of the oxidant include chromium-based oxidants such as pyridinium chlorochromate and pyridinium dichromate, DMSO-based oxidants, manganese-based oxidants, and TEMPO (tetramethylpiperidine oxy radical).

As a series of preferred reaction conditions (reaction temperature, reaction time, and solvent) and preferred purification methods in the scheme, the reaction conditions and the purification methods exemplified in the production method [1] can be used.

[Polymer Compound Containing Structure Unit of Formula (3)]

The present invention relates also to a polymer compound containing a structure unit of Formula (3).

The polymer compound of the present invention is a compound containing a structure unit of Formula (3) and has a weight average molecular weight of preferably 2,000 to 500,000 in terms of polystyrene as measured by gel permeation chromatography.

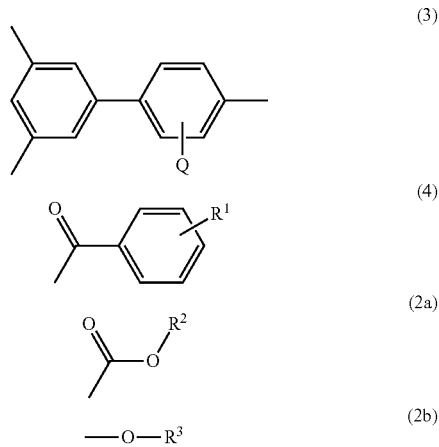

In these formulae, Q is a hydrogen atom or a group of Formula (4) and $R^1$ is a hydrogen atom or a group of Formula (2a) or Formula (2b). In Formula (2a) and Formula (2b), $R^2$ and $R^3$ are independently a hydrogen atom or a $C_{1-6}$ alkyl group. Here, the alkyl group is a linear or branched alkyl group.

In Formula (3), Q is, from the viewpoint of the solubility in a solvent of the polymer compound, preferably a group of Formula (4).

In Formula (4), $R^1$ is, from the viewpoint of the solubility in a solvent and the film formation property of the polymer compound, more preferably a group of Formula (2a) or Formula (2b).

$R^2$ in Formula (2a) and $R^3$ in Formula (2b) are either, from the viewpoint of the condition for the polymerization reaction, desirably an alkyl group or, from the viewpoint of the film formation property of the polymer compound, particularly preferably a hydrogen atom, during the production of the polymer compound containing a structure unit of Formula (3).

The polymer compound of the present invention is a polymer compound containing a structure unit of Formula (3) and may also contain other structure units than the structure unit of Formula (3). Examples of the other structure unit include structure units such as benzene, thiophene, pyridine, and naphthalene. When the polymer compound contains the other structure unit, the polymer compound contains the structure unit of Formula (3) in an amount of desirably 50 mol % to 99 mol %, based on the amount of the whole polymer compound.

On the other hand, a polymer compound consisting only of a structure unit of Formula (3) easily develops the effect of the present invention, so that such a polymer compound is more preferred. Accordingly, the polymer compound of the present invention contains a structure unit of Formula (3) in an amount of desirably 50 mol % to 100 mol %.

[Production Method of Polymer Compound Containing Structure Unit of Formula (3)]

The polymer compound containing a structure unit of Formula (3) can generally be synthesized by a method of a formula according to the following scheme.

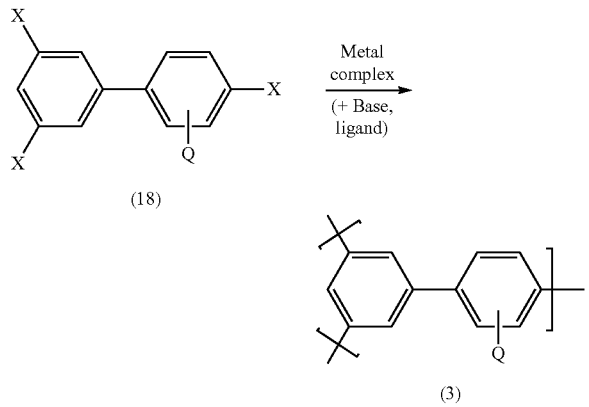

In other words, the polymer compound having a structure unit of Formula (3) can be generally obtained by the polymerization reaction of a compound (monomer) of Formula (18) in the presence of a transition metal complex such as a nickel complex, a palladium complex, and a copper complex and, if necessary, a ligand and a base in a solvent.

In the scheme, X and Q are the same as those defined above.

In the production method, the compounds of Formula (18) may be used individually or in combination of two or more types thereof. When two or more types are used, the ratio of each compound is not particularly limited and can accordingly be controlled according to the structure of the objective polymer.

The polymer compound having a structure unit of Formula (3) may contain other structure units than the structure unit of Formula (3). In this case, besides the compound of Formula (18), an aromatic compound having two or more halogen atoms can be used as another monomer. Another monomer can be used in an amount in a range of 1 mol % to 50 mol %, based on the amount of all monomers used for obtaining the polymer compound of the present invention.

The type of the aromatic compound having two or more halogen atoms is not particularly limited if two or more hydrogen at an arbitrary position of an aromatic ring are substituted with a halogen atom, and the type of aromatic ring may be appropriately selected according to the desired backbone of a polymer. Specific examples of such an aromatic compound include 1,4-dichlorobenzene, 1,3-dichlorobenzene, 1,6-dichloronaphthalene, 2,5-dichlorothiophene, 2,5-dichloropyridine, 2,6-dichloropyridine, 1,4-dibromobenzene, 1,3-dibromobenzene, 1,6-dibromonaphthalene, 2,5-dibromothiophene, 2,5-dibromopyridine, and 2,6-dibromopyridine.

The other monomers (aromatic compounds having two or more halogen atoms) may also be used individually or in an arbitrary combination of two or more types thereof. The ratio thereof is also not particularly limited and can be controlled according to the structure of the objective polymer.

The transition metal complex used in the polymerization reaction is not particularly limited and can optionally be selected from various publicly known metal complexes for polymerization to be used. Examples thereof include reduction catalysts such as copper complexes, nickel complexes, and palladium complexes. Among them, preferred are nickel complexes and palladium complexes. These catalysts may be used individually or in combination of two or more types thereof.

Examples of the nickel complex include tetrakis(triphenylphosphine)nickel, dichloro(2,2'-bipyridine)nickel, and bis(1,5-cyclooctadiene)nickel. Among them, in terms of high polymerizability, preferred is a zero-valence nickel complex such as bis(1,5-cyclooctadiene)nickel. Here, the nickel complexes may be used individually or in combination of two or more types thereof. Moreover, a combination of dichlorobis(triphenylphosphine)nickel(II) and metal zinc as a reductant may also be used.

Examples of the palladium complex include tetrakis(triphenylphosphine)palladium and dichloro{1,3-bis(diphenylphosphine)propane}palladium. Among them, preferred is tetrakis(triphenylphosphine)palladium. Here, the palladium complexes may be used individually or in combination of two or more types thereof.

The metal complex can be used at a molar ratio of $2 \times 10^{-3}$ to $2 \times 10^{-2}$ times the amount of the monomer as a raw material. In the case of a metal complex that itself acts as a reactant such as a zero-valence nickel complex, the metal complex can be used at a molar ratio of 1 to 5 times the amount of the monomer as a raw material.

In the polymerization reaction, if necessary, a ligand and/or a base can be also used depending on the reaction condition.

Examples of the compound becoming a ligand include ligands such as PPh$_3$ (triphenylphosphine), (Tol)$_3$P (tritolylphosphine), (tert-Bu)$_3$P (tri-tert-butylphosphine), (Cy)$_3$P (tricyclohexylphosphine), dppe (1,2-bis(diphenylphosphino)ethane), dppp (1,3-bis(diphenylphosphino)propane), dppf (1,1'-bis(diphenylphosphino)ferrocene), cod (1,5-cyclooctadiene), and bipyridine.

The base may be used either as it is or in an aqueous solution state thereof. Preferred examples of the base include, besides sodium hydride, potassium hydride, butyllithium, and tert-butoxy potassium, inorganic bases such as sodium hydroxide, potassium hydroxide, lithium hydroxide, sodium carbonate, sodium hydrogen carbonate, potassium hydrogen carbonate, potassium phosphate, potassium carbonate, and cesium carbonate, and organic bases, for example aliphatic amines such as triethylamine and diisopropylethylamine, and aromatic amines such as pyridine, quinoline, and imidazole.

The procedure of the polymerization is not particularly limited. However, a monomer is normally dissolved or dispersed in a solvent in a reaction vessel and, thereto, a catalyst and, if necessary, a ligand or a base are added to initiate the reaction.

The type of the solvent used for the polymerization reaction is not particularly limited so long as the solvent can suitably dissolve or disperse the monomer and does not cause an undesirable side reaction between the monomer and a polymer compound generated during the reaction. Examples of the solvent include alcohols, aprotic polar organic solvents (such as DMF, DMSO, DMAc, and NMP), ethers (such as Et$_2$O, i-Pr$_2$O, TBME, CPME, THF, and dioxane), aliphatic hydrocarbons (such as pentane, hexane, and petroleum ether), aromatic hydrocarbons (such as benzene, toluene, xylene, mesitylene, chlorobenzene, dichlorobenzene, nitrobenzene, and tetralin), halogenated hydrocarbons (such as chloroform, dichloromethane, carbon tetrachloride, and 1,2-dichloroethane), ketones (such as acetone and methyl ethyl ketone), lower aliphatic acid esters (such as methyl acetate, ethyl acetate, butyl acetate, and methyl propionate), and nitriles (such as acetonitrile, propionitrile, and butyronitrile). The solvents may be used individually or in an arbitrary combination of two or more types thereof.

The atmosphere for the polymerization reaction is not particularly limited. However, the polymerization reaction is normally effected in air or in an inactive atmosphere, preferably in an inactive atmosphere. Examples of the inactive atmosphere include an argon atmosphere and a nitrogen atmosphere.

The temperature for the polymerization reaction is not particularly limited. However, the temperature is −20° C. to 100° C., preferably 20° C. to 60° C. The pressure for the polymerization reaction is not also particularly limited. However, the polymerization reaction is normally performed under normal pressure.

The time for the polymerization reaction varies depending on the type of used monomers and catalysts, the temperature and the pressure for the polymerization reaction, and the like. However, the time is 1 hour to 1,000 hours, preferably 2 hours to 20 hours.

After the completion of the polymerization reaction, the obtained polymer compound is recovered by an optional method and, if necessary, the polymer compound is subjected to a post-treatment such as washing. Examples of the method for recovering the polymer compound from the reaction solution include reprecipitation.

Examples of the post-treatment include removal of a metal complex by washing with an acid such as hydrochloric acid or a chelating agent.

The thus obtained polymer compound having a structure unit of Formula (3) can be dissolved in various solvents and, moreover, the solution obtained from the dissolution of the polymer compound in a solvent has a low viscosity and excellent handling properties, so that the polymer compound can suitably be applied to various materials in the state of "solution of the polymer compound".

Then, by applying or adsorbing the solution on or to a solid-phase carrier, there can be obtained a coating film containing the polymer compound having a structure unit of Formula (3).

The solid-phase carrier means a solid that can be coated with the polymer compound of the present invention having a structure unit of Formula (3) by applying or adsorbing the polymer compound on or to the solid. The material, the shape, the dimension, and the like of the solid-phase carrier are not particularly limited and an arbitrary solid can be used as the solid-phase carrier.

Specific examples of the material for the solid-phase carrier include: various resin materials such as polyolefin, polystyrene, polyethylene, polycarbonate, polyamide, polyester, and acrylic resin; and inorganic materials such as glass, alumina, carbon, and metal. Examples of the shape of the solid-phase carrier include a plate shape, a particle shape, a fiber shape, a film shape, and a sheet shape.

The materials for the solid-phase carrier may be used individually or in either an arbitrary combination of or a combination at a specific ratio of two or more types thereof according to the material, the shape, the dimension, or the like. Examples of the solid-phase carrier include plate-shaped glasses, sheet-shaped resins, film-shaped resins, laminate plates of an inorganic material and a resin material, particle-shaped or fiber-shaped single substances of various materials or mixtures thereof, and mixtures of a film-shaped resin with an inorganic material.

Examples of the method of applying a solution of the polymer compound of the present invention having a structure unit of Formula (3) on the solid-phase carrier for coating the solid-phase carrier with the polymer compound include an impregnation method, a brushing method, a casting method, and a spin coating method.

The polymer compound of the present invention containing a structure unit of Formula (3) has excellent transparency, excellent heat resistance, and a high refractive index, so that suitable examples of the application thereof include optoelectronic materials for which a high quality performance with respect to such characteristics is required.

In this case, by applying the solution of the polymer compound on a substrate (such as a silicon/silicon dioxide coated substrate, a silicon nitride substrate, a substrate coated with a metal such as aluminum, molybdenum, and chromium, a glass substrate, a quartz substrate, and an ITO substrate) using a spin coating method, a casting method, an inkjet printing method, a spray applying method, or the like; predrying the solution using a hot plate or an oven to form a coating film; and subjecting the coating film to a heating treatment, there can be formed a cured film for the application to various optoelectronic materials.

[Thermocurable Film Forming Polymer Composition]

The present invention relates also to a thermocurable film forming polymer composition containing: as the component (A), a polymer compound containing a structure unit of Formula (19) below among the above polymer compounds having a biphenylene skeleton; as the component (B), a crosslinkable compound; and if desired, a solvent and other additives.

Hereinafter, the detail of each component of the thermocurable film forming polymer composition is described.

<Component (A)>

[Polymer Compound Containing Structure Unit of Formula (19)]

In the present invention, the component (A) is a polymer compound having a biphenylene skeleton, that is, a polymer compound containing a structure unit of Formula (19):

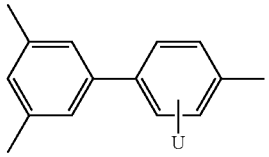

(19)

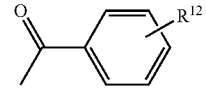

(20)

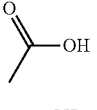

(20a)

—OH (20b)

and having a weight average molecular weight of preferably 2,000 to 500,000 in terms of polystyrene as measured by gel permeation chromatography.

In Formulae, U is a group of Formula (20) and $R^{12}$ is a group of Formula (20a) or Formula (20b).

The structure unit of Formula (19) has such a characteristic as easily obtaining the solubility in a solvent and a high refractive index of the polymer compound.

In Formula (20), $R^{12}$ is more preferably a group of Formula (20a) from the viewpoint of the solubility in a solvent, the thermocurable property, and the film formation property of the polymer compound.

The polymer compound as the component (A) used in the present invention is a polymer compound containing a structure unit of Formula (19) and may also contain other structure units than the structure unit of Formula (19). Examples of the other structure unit include structure units such as benzene, thiophene, pyridine, and naphthalene. When the polymer compound contains the other structure unit, the polymer compound contains the structure unit of Formula (19) in an amount of desirably 50 mol % to 99 mol %, based on the amount of the whole polymer compound.

On the other hand, when the polymer compound as the component (A) is a polymer compound consisting only of the structure unit of Formula (19), the polymer compound easily develops the effect of the present invention, so that such a polymer compound is more preferred. Accordingly, the polymer compound as the component (A) of the present invention contains the structure unit of Formula (19) in an amount of desirably 50 mol % to 100 mol %.

<Component (B)>

The crosslinkable compound as the component (B) of the present invention is a compound having two or more functional groups that can be reacted with the polymer compound containing a structure unit of Formula (19). Examples of such a functional group include an epoxy group, an oxetanyl group, a N-methylol group, and an isocyanate group.

Examples of the compound having two or more epoxy groups or oxetanyl groups include tris(2,3-epoxypropyl)isocyanurate, 1,4-butanediol diglycidyl ether, 1,2-epoxy-4-(epoxyethyl)cyclohexane, glycerol triglycidyl ether, diethylene glycol diglycidyl ether, 2,6-diglycidyl phenylglycidyl ether, 1,1,3-tris[p-(2,3-epoxypropoxy)phenyl]propane, 1,2-cyclohexanedicarboxylic acid diglycidyl ester, 4,4'-methylenebis (N,N-diglycidylaniline), 3,4-epoxycyclohexylmethyl, 3,4-epoxycyclohexane carboxylate, trimethylolethane triglycidyl ether, bisphenol A diglycidyl ether, pentaerythritol polyglycidyl ether, 1,4-bis(3-ethyl-3-oxetanylmethoxymethyl)benzene, and 1,4-bis(3-ethyl-3-oxetanylmethoxymethyl)cyclohexane.

In terms of easy availability, commercially available compounds may also be used. Specific examples (trade names) thereof include the following products to which the specific examples are not limited. Epoxy resins having an amino group such as YH-434 and YH434L (manufactured by Tohto Kasei Co., Ltd.; epoxy resins having a cyclohexene oxide structure such as Epolead GT-401, GT-403, GT-301, and GT-302, Celloxide 2021 and 3000 (manufactured by Daicel Chemical Industries, Ltd.); bisphenol A type epoxy resins such as Epikote 1001, 1002, 1003, 1004, 1007, 1009, 1010, and 828 (manufactured by Japan Epoxy Resins Co., Ltd.); bisphenol F type epoxy resins such as Epikote 807 (manufactured by Japan Epoxy Resins Co., Ltd.); phenol novolak type epoxy resins such as Epikote 152 and 154 (manufactured by Japan Epoxy Resins Co., Ltd.) and EPPN 201 and 202 (manufactured by Nippon Kayaku Co., Ltd.); cresol novolak type epoxy resins such as EOCN-102, EOCN-103S, EOCN-104S, EOCN-1020, EOCN-1025, and EOCN-1027 (manufactured by Nippon Kayaku Co., Ltd.) and Epikote 180S75 (manufactured by Japan Epoxy Resins Co., Ltd.); alicyclic epoxy resins such as Denacol EX-252 (manufactured by Nagase ChemteX Corporation), CY175 CY177, and CY179, and Araldite CY-182, CY-192, and CY-184 (manufactured by CIBA-GEIGY A.G.), Epiclon 200 and 400 (manufactured by DIC Corporation), Epikote 871 and 872 (manufactured by Japan Epoxy Resins Co., Ltd.), ED-5661 and ED-5662 (manufactured by Celanese Coating Co., Ltd.); and aliphatic polyglycidyl ethers such as Denacol EX-611, EX-612, EX-614, EX-622, EX-411, EX-512, EX-522, EX-421, EX-313, EX-314, and EX-321 (manufactured by Nagase ChemteX Corporation).

As the compound having two or more epoxy groups, a polymer having epoxy groups can be used. Such a polymer is not particularly limited to be used so long as the polymer has epoxy groups.

The polymer having epoxy groups can be produced by, for example, an addition polymerization using an addition-polymerizable monomer having an epoxy group. Examples of the polymer having epoxy groups include: addition-polymerized polymers such as copolymers of polyglycidyl acrylate or glycidyl methacrylate with ethyl methacrylate and copolymers of glycidyl methacrylate, styrene, and 2-hydroxyethyl methacrylate; and condensation-polymerized polymers such as epoxy novolak.

The polymer having epoxy groups can also be produced by a reaction of a polymer compound having a hydroxy group with a compound having an epoxy group such as epichlorohydrin and glycidyl tosylate.

Such a polymer has a weight average molecular weight of, for example, 300 to 200,000.

Examples of the compound having two or more N-methylol groups include methoxymethylated glycoluril, methoxymethylated benzoguanamine, and methoxymethylated melamine.

Specific examples of the compound include hexamethoxymethylmelamine, tetramethoxymethylbenzoguanamine, 1,3,4,6-tetrakis(butoxymethyl)glycoluril, 1,3,4,6-tetrakis(hydroxymethyl)glycoluril, 1,3-bis(hydroxymethyl) urea, 1,1,3,3-tetrakis(butoxymethyl)urea, 1,1,3,3-tetrakis (methoxymethyl)urea, 1,3-bis(hydroxymethyl)-4,5-dihydroxy-2-imidazolinone, and 1,3-bis(methoxymethyl)-4,5-dimethoxy-2-imidazolinone.

Examples of the commercially available product thereof include compounds such as methoxymethyl type melamine compounds manufactured by Nihon Cytec Industries, Inc. (trade name: Cymel 300, Cymel 301, Cymel 303, Cymel 350), butoxymethyl type melamine compounds (trade name: Mycoat 506, Mycoat 508), and glycoluril compounds (trade name: Cymel 1170, Powderlink 1174), methylated urea resins (trade name: UFR 65), butylated urea resins (trade name: UFR300, U-VAN 10S60, U-VAN 10R, U-VAN 11HV), and urea/formaldehyde-based resins (highly condensed type) manufactured by DIC Corporation (trade name: Beckamine J-300S, Beckamine P-955, Beckamine N). The compound having two or more N-methylol groups may be a compound obtained by condensing a melamine compound, a urea compound, a glycoluril compound, or a benzoguanamine compound in which a hydrogen atom on an amino group is substituted with a methylol group or an alkoxymethyl group, and examples of such a compound include a macromolecular compound produced from a melamine compound (trade name: Cymel 303) and a benzoguanamine compound (trade name: Cymel 1123) which is described in U.S. Pat. No. 6,323, 310.

Examples of the compound having two or more isocyanate groups include isophoronediisocyanate, 1,6-hexamethylenediisocyanate, methylenebis(4-cyclohexylisocyanate), and trimethylhexamethylenediisocyanate; a dimer and a trimer of these compounds; and reaction products of these compounds with diols, triols, diamines, or triamines.

As the compound having two or more isocyanate groups, there may be used a compound having two or more isocyanate groups blocked with a blocking agent dissociating during baking. Examples of the blocking agent include: alcohols such as methanol, ethanol, isopropanol, n-butanol, 2-ethoxyhexanol, 2-N,N-dimethylaminoethanol, 2-ethoxyethanol, and cyclohexanol; phenols such as phenol, o-nitrophenol, p-chlorophenol, and o-, m-, and p-cresol; lactams such as ε-caprolactam; oximes such as acetone oxime, methyl ethyl ketone oxime, methyl isobutyl ketone oxime, cyclohexanone oxime, acetophenone oxime, and benzophenone oxime; pyrazoles such as pyrazole, 3,5-dimethylpyrazole, and 3-methylpyrazole; and thiols such as dodecanethiol and benzenethiol.

These crosslinkable compounds may be used individually or in combination of two or more types thereof. Among the above crosslinkable compounds, in terms of the reactivity with the group of Formula (2a) or Formula (2b), a crosslinkable compound having two or more epoxy groups or a compound having two or more oxetanyl groups is preferred.

The content of the crosslinkable compound as the component (B) in the thermocurable film forming polymer composition of the present invention is preferably 3 to 50 parts by mass, more preferably 5 to 40 parts by mass, most preferably 10 to 30 parts by mass, relative to 100 parts by mass of the polymer compound as the component (A). When the ratio is excessively low, solvent resistance or heat resistance of a cured film obtained from the thermocurable film forming polymer composition is lowered. On the other hand, when the ratio is excessively high, solvent resistance may be lowered or preservation stability may be lowered.

<Solvent>

One of modes of the thermocurable film forming polymer composition of the present invention is a state of a solution. The solvent used at this time is a solvent capable of dissolving the component (A), the component (B), additives (described below) to be blended in the composition if desired, and the like. The type and the structure of the solvent are not particularly limited so long as the solvent has such a dissolving potential.

Examples of such a solvent include organic solvents such as ethylene glycol monomethyl ether, ethylene glycol monoethyl ether, methylcellosolve acetate, ethylcellosolve acetate, diethylene glycol monomethyl ether, diethylene glycol monoethyl ether, propylene glycol, propylene glycol monomethyl ether, propylene glycol monomethyl ether acetate, propylene glycol propyl ether acetate, toluene, xylene, methyl ethyl ketone, cyclopentanone, cyclohexanone, 2-butanone, 3-methyl-2-pentanone, 2-pentanone, 2-heptanone, γ-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methyl-2-pyrrolidone.

These solvents may be used individually or in combination of two or more types thereof.

Among these solvents, preferred are propylene glycol monomethyl ether, N,N-dimethylacetamide, and N-methyl-2-pyrrolidone from the viewpoint that the solubility of the component (A) in the solvent is high and the coating film property of the composition is advantageous.

<Other Additives>

Further, the thermocurable film forming polymer composition of the present invention may contain, if necessary, a surfactant, an anti-oxidant, a rheology controlling agent, an adhesion assistant such as a silane coupling agent, a pigment, a dye, a preservation stabilizer, an anti-foaming agent, and the like, so long as the effect of the present invention is not impaired.

<Thermocurable Film Forming Polymer Composition>

The thermocurable film forming polymer composition of the present invention is a composition that contains a polymer compound containing a structure unit of Formula (19) as the component (A) and a crosslinkable compound as the component (B) and may contain, if desired, a solvent and one or more type(s) of other additives.

Particularly, a preferred example of the thermocurable film forming polymer composition of the present invention is a thermocurable film forming polymer composition containing 100 parts by mass of the component (A) and 3 to 50 parts by mass of the component (B).

The blending ratio, the preparing method, and the like when the thermocurable film forming polymer composition of the present invention is used as a solution are described in detail below.

The ratio of the solid content in the thermocurable film forming polymer composition of the present invention is not particularly limited so long as each component of the composition is homogeneously dissolved in a solvent. However, the ratio of the solid content is 1 to 80% by mass, preferably 5 to 60% by mass, more preferably 10 to 50% by mass. Here, the solid content means a component remaining after removing the solvent from all components of the thermocurable film forming polymer composition.

The preparing method of the thermocurable film forming polymer composition of the present invention is not particularly limited. However, examples of the preparing method include: a method including dissolving the component (A) in the solvent, and mixing the component (B) at a predetermined ratio with the resultant solution to prepare a homogeneous solution; and a method in which, if necessary, other additives are further added to be mixed with the composition at an appropriate step of the former method.

Then, the prepared solution of the thermocurable film forming polymer composition is preferably filtered using a filter having a pore diameter of around 0.2 µm and the like to be used.

<Coating Film and Cured Film>

A coating film can be formed by applying the thermocurable film forming polymer composition of the present invention on a substrate (such as a silicon/silicon dioxide coated substrate, a silicon nitride substrate, a substrate coated with a metal such as aluminum, molybdenum, and chromium, a glass substrate, a quartz substrate, and an ITO substrate) or a film (for example, resin films such as a triacetyl cellulose film, a polyester film, and an acrylic film) by spin coating, flow coating, roll coating, slit coating, slit coating followed by spin coating, inkjet coating, printing, or the like; and pre-baking the composition on a hot plate, in an oven, or the like. Thereafter, by subjecting the coating film to a heating treatment, a cured film is formed.

As the conditions for the heating treatment, there are adopted a heating temperature and a heating time accordingly selected from, for example, a temperature range of 70° C. to 160° C. and a time range of 0.3 to 60 minutes, respectively. The heating temperature and the heating time are preferably 80° C. to 140° C. and 0.5 to 10 minutes respectively.

The film thickness of the cured film formed from the thermocurable film forming polymer composition is, for example, 0.1 to 50 μm and can be accordingly selected in consideration of the optical and electrical properties and the unevenness of the used substrate.

As the post bake, there is generally adopted a method in which the film is subjected to the treatment at a heating temperature selected from a temperature range of 140° C. to 250° C. for 5 to 30 minutes in the case of the treatment performed on a hot plate, or for 30 to 90 minutes in the case of the treatment performed in an oven.

By curing the thermocurable film forming polymer composition of the present invention under such conditions, there can be formed a curing film having high heat resistance, a high refractive index, high transparency, and solvent resistance.

Therefore, the thermocurable film forming polymer composition of the present invention is suitable as a material for forming a cured film such as a protective film, a planarizing film, and an insulating film in various displays including a light-retrieving efficiency enhancing layer of an LED element or a solid imaging element, a thin-film transistor (TFT) type liquid crystal display element, and an organic EL element.

EXAMPLES

Hereinafter, the present invention will be further described more specifically referring to Examples which should not be construed as limiting the scope of the present invention.

Analysis apparatuses and analysis conditions used in Examples are as follows.
[$^1$H NMR]
Apparatus: Varian NMR System 400NB (400 MHz) JEOL-ECA700 (700 MHz)
Measuring solvent: CDCl$_3$, DMSO-d$_6$
Standard substance: Tetramethylsilane (TMS) (δ 0.0 ppm)
[$^{13}$C NMR]
Apparatus: Varian NMR System 400NB (100 MHz)
Measuring solvent: CDCl$_3$
Standard substance: CDCl$_3$ (δ 77.0 ppm)
[GPC]
Apparatus: HLC-8200 GPC; manufactured by Tosoh Corporation
Column: Shodex KF-804L+KF-805L
Column temperature: 40° C.
Solvent: Tetrahydrofuran
Detector: UV (254 nm)
Calibration curve: Standard polystyrene
[Multiple Angle Light Scattering Detector]
Apparatus: DAWN HELEOS; manufactured by Wyatt Technology Corporation
Solvent: Tetrahydrofuran
[Transmission Type Electron Microscope (TEM)]
Apparatus: H-8000; manufactured by Hitachi, Ltd.
[E Type Viscometer]
Apparatus: VISCONIC ED; manufactured by Tokimec Inc.
Measuring temperature: 25° C.
[Ultraviolet-Visible Spectrophotometer]
Apparatus: SHIMADZU UV-2550; manufactured by Shimadzu Corporation
Wavelength: 400 nm
[Ellipsometer]
Apparatus: Multiple incident angle spectro ellipsometer VASE; manufactured by J. A. Woollam Japan Co., Ltd.
Wavelength: 633 nm
[Prism Coupler]
Apparatus: 2010 PRISM COUPLER; manufactured by Metricon Corporation
Wavelength: 633 nm
[Differential Thermogravimetric Analyzer (TG-DTA)]
Apparatus: TG-8120; manufactured by Rigaku Corporation
Temperature rising rate: 10° C./min
Measuring temperature: 25° C.-500° C.
[Abbreviations Used in Examples]
The meaning of abbreviation symbols used in the following Examples are as follows.
<Epoxy Compound>
CEL: trade name: Celloxide P-2021; manufactured by Daicel Chemical Industries, Ltd. (compound name: 3,4-epoxycyclohexenylmethyl-3',4'-epoxycyclohexene carboxylate)
GT4: trade name: Epolead GT-401; manufactured by Daicel Chemical Industries, Ltd. (compound name: epoxidized butane tetracarboxylic acid tetrakis-(3-cyclohexenylmethyl) modified ε-caprolactone)
BPAG: 2,2-(bis-4-glycidyloxyphenyl)propane
<Solvent>
PGME: propylene glycol monomethyl ether
NMP: N-methyl-2-pyrrolidone
DMF: N,N-dimethylformamide
DMAc: N,N-dimethylacetamide
THF: tetrahydrofuran Example 1

Production of Compound of Formula (1) Using Production Method [1]

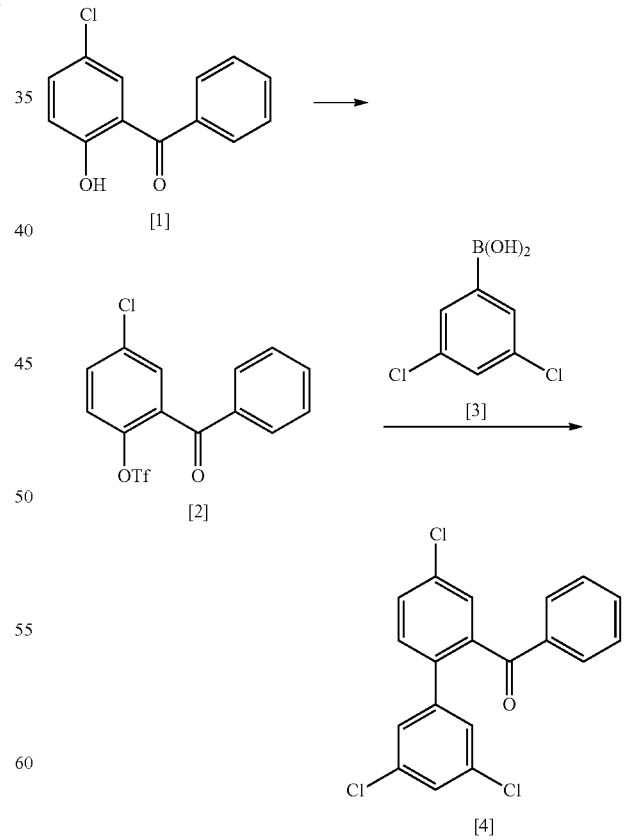

A solution of 5-chloro-2-hydroxybenzophenone [1] (115 g, 0.494 mol) in methylene chloride (640 mL) was cooled down to −10° C. and, thereinto, trifluoromethanesulfonic anhydride (154 g, 0.545 mol) was dropped over 1 hour. Next, into the resultant reaction mixture, at the same temperature, pyridine (46.0 mL, 0.569 mol) was dropped over 1 hour and the reaction was effected at −5° C. for 1 hour. The reaction solution was poured into ice water (2 L) and the organic phase was separated. The aqueous phase was extracted with methylene chloride (200 mL) twice and the organic phases were combined, followed by washing the resultant organic phase with a saturated brine (1 L) twice. The separated organic phase was dried over magnesium sulfate and, from the organic phase, the solvent was distilled off under reduced pressure to obtain a compound [2] (corresponding to the compound of Formula (6), yield amount: 179 g, yield: 99%).

To a solution of the compound [2] (156 g, 0.428 mol) in toluene (1.25 L), sodium carbonate (120 g, 1.13 mol), distilled water (570 mL), lithium chloride (54.5 g, 1.29 mol), 3,5-dichlorophenylboronic acid [3] (corresponding to the compound of Formula (5), 125 g, 0.656 mol), ethanol (125 mL), and tetrakis(triphenylphosphine)palladium (10.9 g, 9.43 mmol) were added and the reaction was effected at 80° C. for 19 hours. The reaction solution was filtered using Celite and the resultant filtrate was phase-separated. The organic phase was washed with a saturated brine (1 L) and was dried over magnesium sulfate and, therefrom, the solvent was distilled off under reduced pressure to obtain a crude product of a compound [4].

The crude product was purified by silica gel column chromatography (weight: 1.5 Kg, hexane/toluene) and, further, was recrystallized in ethanol to obtain a purified product of the compound [4] (corresponding to the compound of Formula (1), yield amount: 95.0 g, yield: 61%).

The measurement results of $^1$H NMR and $^{13}$C NMR of the compound [4] were as follows.

$^1$H NMR (400 MHz, CDCl$_3$): δ 7.62 (dd, J=8.4, 1.6 Hz, 2H), 7.56 (dd, J=8.0, 2.0 Hz, 1H), 7.53 (d, J=2.0 Hz, 1H), 7.49 (tt, J=7.6, 1.6 Hz, 1H), 7.37 (d, J=8.0 Hz, 1H), 7.37-7.32 (m, 2H), 7.15 (t, J=1.6 Hz, 1H), 7.09 (d, J=1.6 Hz, 2H).

$^{13}$C NMR (100 MHz, CDCl$_3$): δ 196.31, 141.78, 140.11, 136.70, 136.53, 134.80, 134.46, 133.53, 131.12, 130.67, 129.64, 128.97, 128.42, 127.61, 127.27.

Example 2

Production of Polymer Compound (Branched) Using Compound [4]

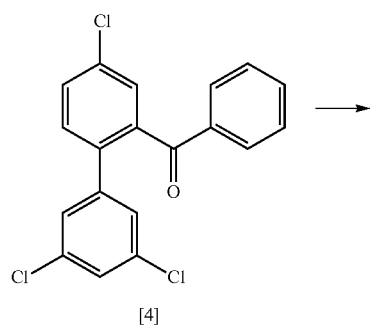

[4] →

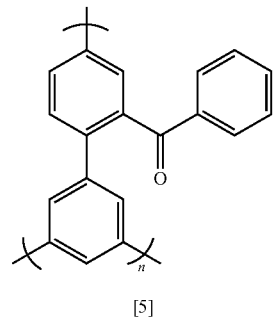

[5]

Into a 500 mL flask equipped with a reflux tower, the compound [4] (10.0 g, 27.7 mmol) obtained in Example 1 was charged and was dissolved in 1,4-dioxane (250 mL). The reaction system was purged with nitrogen and, into the reaction system, 2,2'-bipyridine (manufactured by Kanto Chemical Co., Inc.) (7.79 g, 49.9 mmol), 1,8-cyclooctadiene (manufactured by Kanto Chemical Co., Inc.) (4.50 g, 41.6 mmol), and bis(1,5-cyclooctadiene)nickel (manufactured by Kanto Chemical Co., Inc.) (13.7 g, 49.9 mmol) were charged. The reaction was effected at 60° C. for 1 hour. The reaction solution was cooled down to room temperature and was filtered using Celite 545 and the resultant residue was washed with THF (450 g), followed by distilling off THF and 1,4-dioxane under reduced pressure. To the residue, chloroform (1,500 g) was added and a 30% hydrochloric acid aqueous solution (400 g) and ion-exchanged water (400 g) were added to wash the organic phase. Further, the organic phase was washed with sodium chloride (50 g) and ion-exchanged water (950 g) and was dehydrated with sodium sulfate (80 g). From the organic phase, chloroform was distilled off under reduced pressure. To the resultant residue, THF (36 g) was added and reprecipitation was performed by a 30% hydrochloric acid aqueous solution (250 g) and methanol (750 g). To the resultant colorless solid, THF (15 g) was added and reprecipitation was performed by acetone (300 g). The resultant colorless solid was dried to obtain the objective polymer compound [5] (2.51 g). The measurement result of $^1$H NMR spectrum of the polymer compound [5] is shown in FIG. 1.

The obtained polymer compound [5] is a compound having a structure unit of Formula (3). The weight average molecular weight (Mw) and the degree of distribution (Mw (weight average molecular weight)/Mn (number average molecular weight)) of the polymer compound were measured by gel permeation chromatography and were found to be 76,700 and 3.3, respectively, in terms of polystyrene. The 5% weight decrease temperature of the polymer compound was measured by a differential thermogravimetric analyzer (TG-DTA) and was found to be 460° C. or more.

Example 3

Production of Compound of Formula (1) by Production Method [2]

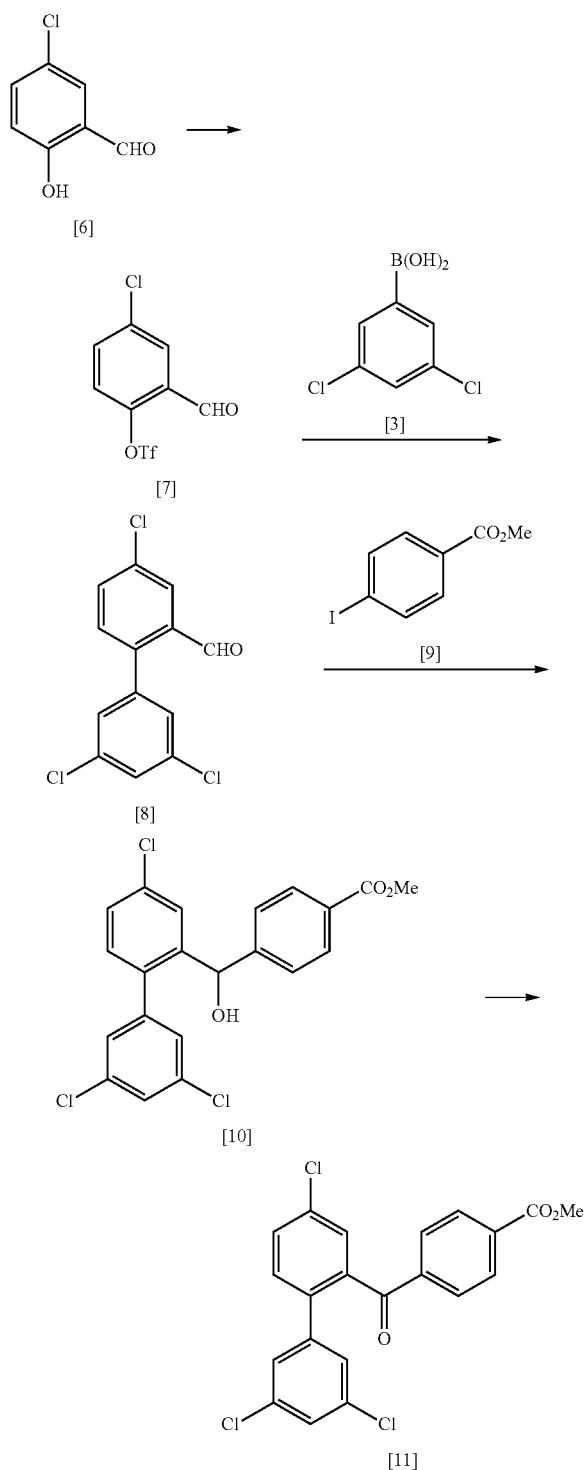

In an argon atmosphere, a solution of 5-chlorosalicylaldehyde [6] (78.9 g, 0.504 mol) in methylene chloride (1.20 L) was cooled down to −10° C. and, thereinto, pyridine (47.3 mL, 0.585 mol) was dropped. Next, the resultant reaction mixture was cooled down to a temperature of −20° C. and, into the reaction mixture, trifluoromethanesulfonic anhydride (156 g, 0.554 mol) was dropped over 20 minutes. At the same temperature, the reaction was effected for 1.5 hour. The reaction solution was poured into distilled water (600 mL) and the organic phase was separated. The aqueous phase was extracted with methylene chloride (600 mL) and the organic phases were combined. The combined organic phase was washed with distilled water (600 mL), saturated aqueous solution of sodium hydrogen carbonate (500 mL), distilled water (600 mL), and a saturated brine (500 mL) in this order. The separated organic phase was dried over magnesium sulfate and, therefrom, the solvent was distilled off under reduced pressure to obtain a compound [7] (corresponding to the compound of Formula (9), yield amount: 145 g, yield: 100%).

The measurement result of NMR of the compound [7] was as follows. $^1$H NMR (400 MHz, CDCl$_3$): δ 10.22 (s, 1H), 7.96 (d, J=2.4 Hz, 1H), 7.68 (dd, J=8.8, 2.4 Hz, 1H), 7.38 (d, J=8.8 Hz, 1H).

In an argon atmosphere, to a solution of the compound [7] (145 g, 0.501 mol) and 3,5-dichlorophenylboronic acid [3] (corresponding to the compound of Formula (5), 100 g, 0.526 mol) in toluene (1.15 L), sodium carbonate (133 g, 1.25 mol), lithium chloride (63.7 g, 1.50 mol), distilled water (870 mL), ethanol (290 mL), and tetrakis(triphenylphosphine)palladium (15.6 g, 13.5 mmol) were added, and the reaction was effected at 80° C. for 44 hours. The reaction mixture was cooled down and, therefrom, insoluble matters were filtered off, followed by washing the insoluble matters with toluene (1 L) and distilled water (500 mL). The obtained filtrate was phase-separated and the aqueous phase was extracted with toluene (1 L). The combined organic phase was washed with distilled water (1 L) twice and with a saturated brine (1 L) and was dried over magnesium sulfate and, therefrom, the solvent was distilled off under reduced pressure to obtain a crude product (weight: 181 g) of the compound [8]. The crude product was refluxed in a solvent mixture of toluene (30 mL) and hexane (460 mL) and was cooled down to 10° C. The solid was collected by filtration and was dried to obtain a purified product of the aldehyde compound [8] (corresponding to the compound of Formula (7), yield amount: 92.0 g, yield: 64%).

The measurement results of $^1$H NMR and $^{13}$C NMR of the aldehyde compound [8] were as follows.

$^1$H NMR (400 MHz, CDCl$_3$): δ 9.92 (s, 1H), 8.00 (d, J=2.4 Hz, 1H), 7.63 (dd, J=8.4, 2.4 Hz, 1H), 7.47 (t, J=2.0 Hz, 1H), 7.36 (d, J=8.4 Hz, 1H), 7.25 (d, J=2.0 Hz, 2H).

$^{13}$C NMR (100 MHz, CDCl$_3$): δ 189.80, 140.91, 139.57, 135.42, 135.29, 134.52, 133.72, 131.93, 128.58, 128.20, 127.95.

In an argon atmosphere, a solution of methyl 4-iodobenzoate [9] (corresponding to the compound of Formula (8), 94.9 g, 0.362 mol) in THF (1.80 L) was cooled down to −20° C. and, thereinto, an isopropyl Grignard reagent (2 mol/L diethyl ether solution, 186 mL, 0.372 mol) was dropped over 30 minutes. After the completion of the dropping, the resultant reaction mixture was stirred at the same temperature for 2 hours and, thereinto, a solution of the aldehyde compound [8] (corresponding to the compound of Formula (7), 89.7 g, 0.314 mol) in THF (660 mL) was dropped over 45 minutes. Thereafter, the reaction was effected at the same temperature for 1 hour. To the reaction solution, a saturated ammonium chloride aqueous solution (1 L) was added and the organic phase was separated. The organic phase was washed with a saturated brine (400 mL) four times and, therefrom, the solvent was distilled off under reduced pressure. The resultant residue was subjected to azeotropy with toluene (100 mL) three times to obtain a crude product of the compound [10] (corresponding to the compound of Formula (10), 148 g).

The measurement result of $^1$H NMR of the compound [10] was as follows.

$^1$H NMR (400 MHz, CDCl$_3$): δ 7.92 (d, J=8.4 Hz, 2H), 7.58 (d, J=2.0 Hz, 1H), 7.36 (t, J=2.0 Hz, 1H), 7.33 (dd, J=8.4, 2.0 Hz, 1H), 7.16 (d, J=8.4 Hz, 2H), 7.11 (d, J=8.4 Hz, 1H), 7.04 (d, J=2.0 Hz, 2H), 5.81 (s, 1H), 3.89 (s, 3H), 2.62 (bs, 1H).

To a methylene chloride (900 mL) solution containing potassium bromide (3.75 g, 31.5 mmol), 2,2,6,6-tetramethylpiperidine 1-oxyl (TEMPO, 0.500 g, 3.20 mmol), and the crude product of the compound [10] (corresponding to the compound of Formula (10), 148 g) obtained in the above reaction, a saturated sodium hydrogen carbonate aqueous solution (900 mL) was added. The resultant reaction mixture was cooled down with salt ice water and, thereinto, a sodium hypochlorite solution (350 g) was dropped over 30 minutes. After the completion of the dropping, the reaction was effected for 1 hour. The reaction solution was phase-separated and the separated organic phase was washed with distilled water (600 mL) twice, then with a saturated brine (600 mL). Therefrom, the solvent was distilled off under reduced pressure to obtain a solid (173 g). The solid (173 g) was dissolved in ethyl acetate (500 mL) and methylene chloride (166 mL) and, to the resultant solution, 7 g of activated carbon powder was added. The resultant mixture was stirred for 30 minutes and was filtered using Celite. This activated carbon treatment and Celite filtration were repeated until the color of the filtrate disappeared (three times). The filtrate was concentrated under reduced pressure and the resultant residue (151 g) was recrystallized using ethyl acetate (300 mL) and hexane (1.50 L) to obtain a compound [11] (corresponding to the compound of Formula (1), yield amount: 109 g, yield from the compound [8]: 82%).

The measurement results of $^1$H NMR and $^{13}$C NMR of the compound [11] were as follows.

$^1$H NMR (400 MHz, CDCl$_3$): δ 7.98 (d, J=8.4 Hz, 2H), 7.64 (d, J=8.4 Hz, 2H), 7.60 (dd, J=8.4, 2.0 Hz, 1H), 7.55 (d, J=2.0 Hz, 1H), 7.39 (d, J=8.4 Hz, 1H), 7.15 (t, J=1.6 Hz, 1H), 7.07 (d, J=1.6 Hz, 2H), 3.93 (s, 3H).

$^{13}$C NMR (100 MHz, CDCl$_3$): δ 195.85, 165.90, 141.48, 139.87, 139.52, 136.68, 134.95, 134.72, 133.99, 131.17, 131.11, 129.54, 129.31, 129.11, 127.80, 127.23, 52.47.

Example 4

Production of Polymer Compound (Branched) Using Compound [11]

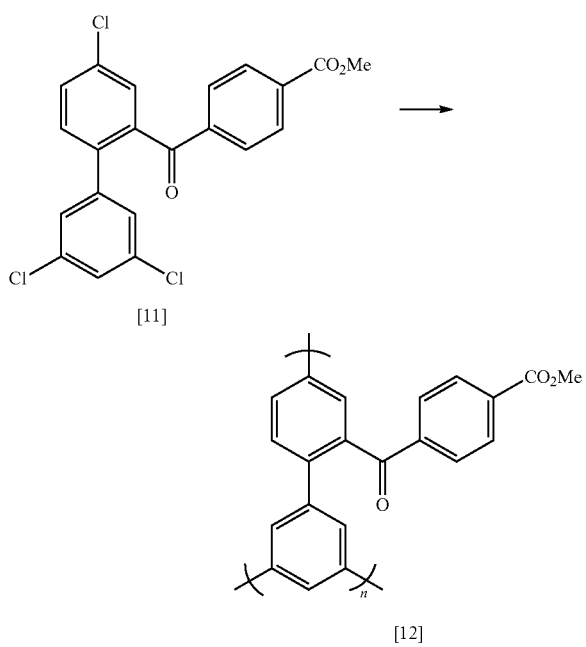

Into a 1 L flask equipped with a reflux tower, the compound [11] (25.0 g, 59.6 mmol) obtained in Example 3 was charged and was dissolved in 1,4-dioxane (744 mL). The reaction system was purged with nitrogen and, into the reaction system, 2,2'-bipyridine (manufactured by Kanto Chemical Co., Inc.) (16.7 g, 107 mmol), 1,8-cyclooctadiene (manufactured by Kanto Chemical Co., Inc.) (9.7 g, 89.4 mmol), and bis(1,5-cyclooctadiene)nickel (manufactured by Kanto Chemical Co., Inc.) (29.5 g, 107 mmol) were charged. The reaction was effected at 40° C. for 5 hours. The reaction mixture was left to be cooled down to room temperature and, thereto, chloroform (1,350 g), a 30% hydrochloric acid aqueous solution (500 g), and ion-exchanged water (1,500 g) were added to wash the organic phase. Further, to the reaction mixture, a 30% hydrochloric acid aqueous solution (500 g) and ion-exchanged water (1,500 g) were added to wash the organic phase. The organic phase was washed with ion-exchanged water (1,500 g) again. From the organic phase, chloroform and 1,4-dioxane were distilled off under reduced pressure and, to the resultant residue, THF (42 g) was added, followed by performing reprecipitation by methanol (1,400 g). The resultant colorless solid was dried to obtain the objective compound [12] (19.3 g). The measurement result of $^1$H NMR spectrum of the compound [12] is shown in FIG. 2.

The obtained polymer compound [12] is a compound having a structure unit of Formula (3). The weight average molecular weight (Mw) and the degree of distribution (Mw/Mn) of the polymer compound were measured by gel permeation chromatography and were found to be 9,900 and 2.3, respectively, in terms of polystyrene. The 5% weight decrease temperature of the polymer compound was measured by a differential thermogravimetric analyzer (TG-DTA) and was found to be 363° C.

Example 5

Conversion of Methoxycarbonyl Group to Carboxy Group

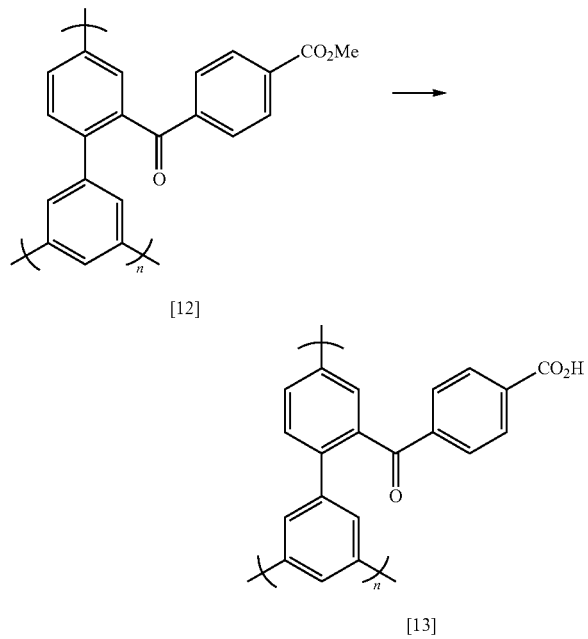

Example 6

Production of Compound of Formula (1) by Production Method [2]

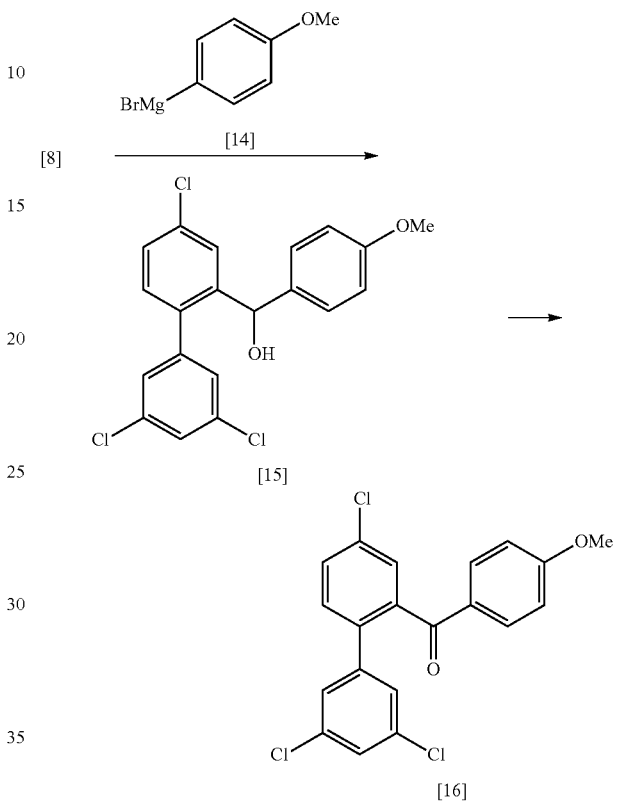

Into a 1 L flask equipped with a reflux tower, the compound [12] (13.0 g) obtained in Example 4 was charged and was dissolved in THF (260 mL). The reaction system was purged with nitrogen and, into the reaction system, lithium hydroxide monohydrate (manufactured by Kanto Chemical Co., Inc.) (5.2 g, 123 mmol) and ion-exchanged water (26 g) were charged. The reaction was effected at 70° C. for 1 hour. The reaction mixture was left to be cooled down to room temperature and, thereto, a 30% hydrochloric acid aqueous solution (66 g) was added. The resultant reaction mixture was reprecipitated by methanol (1,000 g). The resultant colorless solid was dissolved in THF (45 g) and the resultant reaction mixture was reprecipitated by ion-exchanged water (500 g). The resultant colorless solid was dried to obtain the objective compound [13] (corresponding to the polymer compound having a structure unit of Formula (19)) (8.2 g). The measurement result of $^1$H NMR spectrum of the compound [13] is shown in FIG. 3. According to FIG. 3, a peak at around 3.7 ppm ascribed to a methyl group appearing in FIG. 2 ($^1$H NMR spectrum of the compound [12]) disappears in FIG. 3, so that the methyl group was substituted with a hydrogen atom.

The weight average molecular weight (Mw) and the degree of distribution (Mw/Mn) of the obtained polymer compound [13] were measured by gel permeation chromatography and were found to be 10,300 and 2.6, respectively, in terms of polystyrene.

In a nitrogen atmosphere, a solution of the aldehyde compound [8] (corresponding to the compound of Formula (7), 2.00 g, 7.00 mmol) in THF (6.50 mL) was cooled down to 0° C. and, thereinto, a 4-methoxyphenyl Grignard reagent [14] (corresponding to the compound of Formula (8), 0.5 mol/L THF solution, 16.8 mL, 8.40 mmol) was dropped over 20 minutes. After the completion of the dropping, the resultant reaction mixture was stirred at room temperature for 30 minutes. The reaction solution was cooled down to 0° C. and, thereto, a saturated ammonium chloride aqueous solution (20 mL) was added to quench the reaction. To the reaction mixture, ethyl acetate (20 mL) was added and the organic phase was separated. The aqueous phase was re-extracted with ethyl acetate (20 mL). The organic phases were combined and the combined organic phase was washed with distilled water (30 mL). The organic phase was dried over magnesium sulfate and, therefrom, the solvent was distilled off under reduced pressure. The crude product was purified by silica gel column chromatography (hexane/1,2-dichloroethane) to obtain a compound [15] (corresponding to the compound of Formula (10), yield amount: 2.28 g, yield: 83%).

The measurement result of $^1$H NMR of the compound [15] was as follows.

$^1$H NMR (400 MHz, CDCl$_3$): δ 7.76 (d, J=2.0 Hz, 1H), 7.33 (t, J=2.0 Hz, 1H), 7.31 (dd, J=8.0, 2.0 Hz, 1H), 7.06 (d, J=8.0 Hz, 1H), 6.96 (d, J=8.4 Hz, 2H), 6.93 (d, J=2.0 Hz, 2H), 6.79 (d, J=8.4 Hz, 2H), 5.68 (d, J=3.2 Hz, 1H), 3.78 (s, 3H), 2.13 (d, J=3.2 Hz, 1H).

To a methylene chloride (13.7 mL) solution containing potassium bromide (69.1 mg, 0.580 mmol), 2,2,6,6-tetramethylpiperidine 1-oxyl (TEMPO, 9.10 mg, 0.0580 mmol), and the compound [15] obtained in the above reaction (2.28 g, 5.80 mmol), a saturated sodium hydrogen carbonate aqueous solution (13.7 mL) was added. The resultant reaction mixture was cooled down with salt ice water and, thereinto, a sodium hypochlorite solution (6.48 g) was dropped. After the completion of the dropping, the reaction was effected at the same temperature for 30 minutes and further at room temperature for 1 hour. The reaction solution was phase-separated and the separated organic phase was washed with a saturated brine (10 mL) three times. Therefrom, the solvent was distilled off under reduced pressure to obtain a crude product of the objective compound [16]. The crude product was purified by silica gel column chromatography (hexane/1,2-dichloroethane) to obtain the compound [16] (corresponding to the compound of Formula (1), yield amount: 1.90 g, yield: 84%).

The measurement results of $^1$H NMR and $^{13}$C NMR of the compound [16] were as follows.

$^1$H NMR (400 MHz, CDCl$_3$): δ 7.63 (d, J=9.2 Hz, 2H), 7.54 (dd, J=8.4, 2.4 Hz, 1H), 7.48 (dd, J=2.4, 0.4 Hz, 1H), 7.36 (dd, J=8.4, 0.4 Hz, 1H), 7.18 (t, J=2.0 Hz, 1H), 7.12 (d, J=2.0 Hz, 2H), 6.83 (d, J=9.2 Hz, 2H), 3.84 (s, 3H).

$^{13}$C NMR (100 MHz, CDCl$_3$): δ 194.72, 163.87, 141.88, 140.52, 136.35, 134.77, 134.34, 132.19, 131.10, 130.27, 129.41, 128.64, 127.62, 127.19, 113.75, 55.48.

Example 7

Production of Polymer Compound (Branched) Using Compound [16]

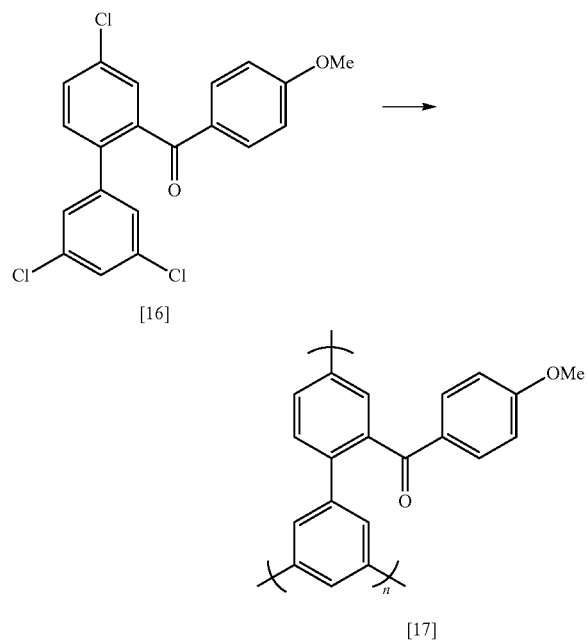

Into a 1 L flask equipped with a reflux tower, 15.0 g of the compound [16] (38.3 mmol) obtained in Example 6 was charged and was dissolved in 1,4-dioxane (450 mL). The inside of the reaction system was purged with nitrogen and, into the reaction system, 10.7 g of 2,2'-bipyridine (manufactured by Kanto Chemical Co., Inc.) (68 mmol), 6.17 g of 1,8-cyclooctadiene (manufactured by Kanto Chemical, Co., Inc.) (57.0 mmol), and 18.8 g of bis(1,5-cyclooctadiene) nickel (manufactured by Kanto Chemical Co., Inc.) (68.4 mmol) were charged. The reaction was effected at 40° C. for 6 hours. The reaction mixture was left to be cooled down to room temperature and, thereto, 620 g of chloroform, 300 g of a 30% hydrochloric acid aqueous solution, and 1,500 g of ion-exchanged water were added to wash the organic phase. Further, to the reaction mixture, 300 g of a 30% hydrochloric acid aqueous solution and 1,000 g of ion-exchanged water were added to wash the organic phase. The organic phase was washed again with 1,000 g of ion-exchanged water. From the organic phase, chloroform and 1,4-dioxane were distilled off under reduced pressure and, to the resultant residue, 36 g of THF was added, followed by performing reprecipitation by 1,000 g of methanol. The resultant colorless solid was dried to obtain the objective polymer compound [17] (10.6 g). The measurement result of $^1$H NMR spectrum of the polymer compound [17] is shown in FIG. 4.

The polymer compound [17], thus obtained, possesses a structure unit of Formula (3). The weight average molecular weight (Mw) and the degree of distribution (Mw/Mn) of the polymer compound were measured by gel permeation chromatography and were found to be 15,000 and 4.4, respectively, in terms of polystyrene.

Example 8

Production Method of Compound of Formula (18)

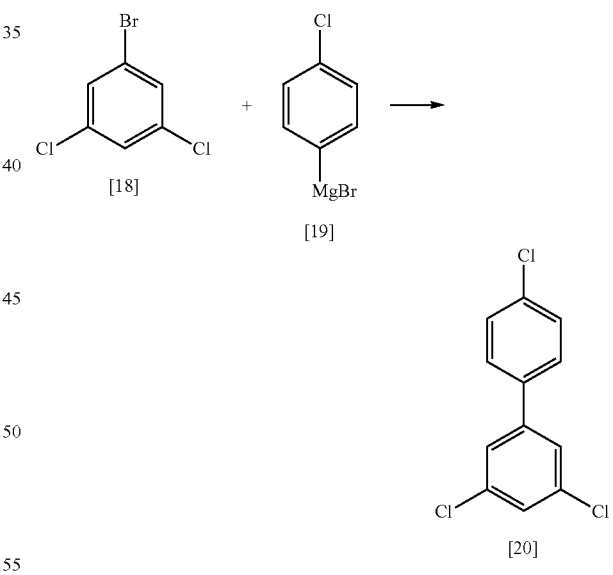

In a nitrogen atmosphere, to a solution of 1-bromo-3,5-dichlorobenzene [18] (15.3 g, 67.9 mmol) in THF (678 mL), a 4-chlorophenyl Grignard reagent [19] (1 mol/L diethyl ether solution, 71.3 mL, 71.3 mmol) and tetrakis(triphenylphosphine)palladium (7.84 g, 6.79 mmol) were added. The temperature of the resultant reaction solution was elevated to 50° C. and the reaction was effected for 16 hours. To the reaction solution, a 20% ammonium chloride aqueous solution (750 mL) was added to quench the reaction. To the reaction mixture, ethyl acetate (2.25 L) was added and the reaction mixture was phase-separated. The separated organic phase was washed with a saturated brine (750 mL) and was dried over magnesium sulfate. From the organic phase, the solvent was distilled off under reduced pressure to obtain a crude product of a compound [20]. The crude product was purified by silica gel column chromatography using 1,2-dichloroethane and hexane to obtain the compound [20] (yield amount: 16.0 g, yield: 92%).

The measurement results of $^1$H NMR and $^{13}$C NMR of the compound [20] were as follows.

$^1$H NMR (400 MHz, CDCl$_3$): δ 7.49-7.37 (m, 6H), 7.35 (t, J=2.4 Hz, 1H).

$^{13}$C NMR (100 MHz, CDCl$_3$): δ 142.81, 136.85, 135.38, 134.66, 129.18, 128.23, 127.42, 125.39.

Example 9

Production of Polymer Compound (Branched) Using Compound [20]

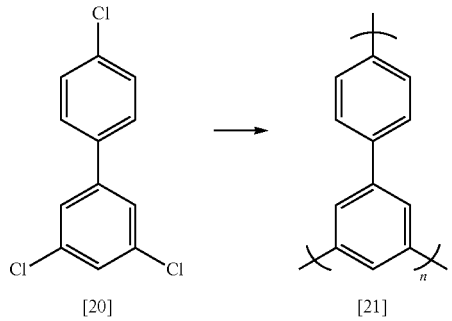

Into a 300 mL flask equipped with a reflux tower, the compound [20] (5.00 g, 19.4 mmol) obtained in Example 8 was charged and was dissolved in 1,4-dioxane (100 mL). The inside of the reaction system was purged with nitrogen and, into the reaction system, 2,2'-bipyridine (manufactured by Kanto Chemical Co., Inc.) (5.50 g, 35.0 mmol), 1,8-cyclooctadiene (manufactured by Kanto Chemical Co., Inc.) (3.20 g, 29 mmol), and bis(1,5-cyclooctadiene)nickel (manufactured by Kanto Chemical Co., Inc.) (9.60 g, 35 mmol) were charged. The reaction was effected at 40° C. for 5 hours. The reaction mixture was left to be cooled down to room temperature and, thereto, chloroform (300 g), a 30% hydrochloric acid aqueous solution (120 g), and ion-exchanged water (120 g) were added to wash the organic phase. From the organic phase, a solid insoluble in chloroform was filtered off and, to the organic phase, a 30% hydrochloric acid aqueous solution (120 g) and ion-exchanged water (120 g) were added to wash the organic phase. The organic phase was reprecipitated by methanol (500 g) and the resultant colorless solid was dissolved by adding TI-IF (15 g) to the solid. The resultant solution was reprecipitated by acetone (100 g). The resultant colorless solid was dried to obtain the objective polymer compound [21] (1.10 g). The measurement result of $^1$H NMR spectrum of the polymer compound [21] is shown in FIG. 5.

The obtained polymer compound [21] is a polymer compound having a structure unit of Formula (3). The weight average molecular weight (Mw) and the degree of distribution (Mw/Mn) of the polymer compound [21] were measured by gel permeation chromatography and were found to be 5,100 and 1.6, respectively, in terms of polystyrene. The 5% weight decrease temperature of the polymer compound was measured by a differential thermogravimetric analyzer (TG-DTA) and was found to be 500° C. or more.

Comparative Example 1

Synthesis of Benzophenone Type Linear Polymer Compound

In a nitrogen atmosphere, a suspension of sodium iodide (0.180 g, 1.20 mmol), triphenylphosphine (0.787 g, 3.00 mmol), dichlorobis(triphenylphosphine)nickel (0.146 g, 0.224 mmol), and activated zinc (0.737 g, 11.3 mmol) in N-methylpyrrolidinone (11.1 mL) was stirred for 5 minutes and, to the suspension, 2-benzoyl-1,4-dichlorobenzene [23] (1.00 g, 4.00 mmol) of Formula below and meta-dichlorobenzene [22] (0.588 g, 4.00 mmol) of Formula below were added. The temperature of the resultant reaction solution was elevated to 70° C. and the reaction was effected for 24 hours. The reaction solution was cooled down to room temperature and was poured into a solvent mixture of ethanol (40 mL) and concentrated hydrochloric acid (1.4 mL) to quench the reaction. To a solid obtained by filtering the reaction solution, ethanol (20 mL) was added and the resultant reaction mixture was stirred for 10 minutes under heating-reflux. The reaction mixture was cooled down to room temperature and was filtered to obtain a crude product. The crude product was dissolved in THF (9 mL) and the resultant solution was reprecipitated by methanol (36 mL). The resultant solid was dried to obtain a linear polymer compound ([24], 0.759 g) of Comparative Example. The measurement result of $^1$H NMR spectrum of the linear polymer compound is shown in FIG. 6.

The weight average molecular weight (Mw) and the degree of distribution (Mw/Mn) of the linear polymer compound were measured by gel permeation chromatography and were found to be 14,200 and 2.8, respectively, in terms of polystyrene.

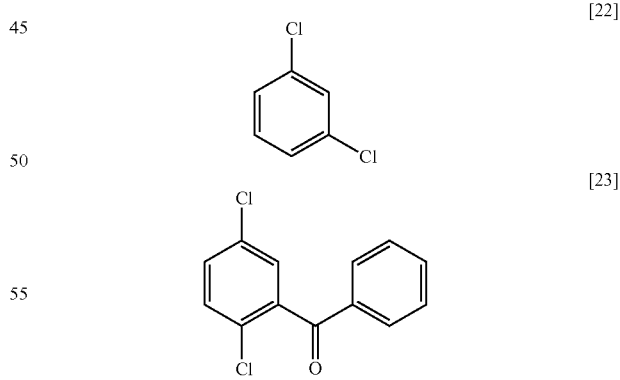

[Physical Property Evaluation of Polymer Compound]
<Solubility of Polymer Compound>

Solubilities of the polymer compounds (branched) and the linear polymer compound obtained in the above Example in various organic solvents were compared with each other. Here, the evaluation was performed at a concentration of 0.2 g/mL and at a temperature of 25° C.

TABLE 1

| Solvent | Polymer ([ ] is compound No.) | | | | Linear polymer |
|---|---|---|---|---|---|
| | Example 2 [5] | Example 4 [12] | Example 5 [13] | Example 7 [17] | Comparative Example 1 [24] |
| DMF | A | A | A | A | B |
| THF | A | A | A | A | B |
| NMP | B | A | A | A | B |
| DMAc | A | A | A | A | B |
| Dimethoxyethane | A | A | A | B | C |
| PGME | C | C | A | C | C |

A: Perfectly dissolved
B: White turbidity was caused or undissolved matter slightly remained
C: Hardly dissolved There was obtained the result that, in comparison with the linear polymer compound of Comparative Example 1, the polymer compounds of Examples 2, 4, 5, and 7 have excellent solubilities in many solvents.

<Viscosity of Polymer Compound>

A 10% by weight NMP solution of each of the polymer compounds obtained in Examples 2, 4, 5, and 7 and the linear polymer compound obtained in Comparative Example 1 was prepared and the viscosity of each solution was measured using an E type viscometer.

TABLE 2

| | Mw | Viscosity [mPa·s] |
|---|---|---|
| Example 2 (compound [5]) | 76,700 | 12.7 |
| Example 4 (compound [12]) | 9,900 | 5.2 |
| Example 5 (compound [13]) | 10,300 | 8.2 |
| Example 7 (compound [17]) | 15,000 | 5.7 |
| Comparative Example 1 (compound [24]) | 14,200 | 18.7 |

As shown in Table 2, there was obtained the result that, in comparison with the linear polymer compound of Comparative Example 1, the polymer compounds of Examples 2, 4, 5, and 7 have lower viscosities.

<Transparency of Polymer Compound>

The polymer compound [5] obtained in Example 2 was dissolved in DMAc and the polymer compound [13] obtained in Example 5 was dissolved in PGME to prepare each solution with a concentration of 15% by weight.

Each solution was applied on a quartz substrate using a spin coater and was subjected to baking on a hot plate at a temperature of 110° C. for 120 seconds to form a coating film having a film thickness of 1.5 µm. The transmittance of the coating film at a wavelength of 400 nm was measured.

Next, the coating film was subjected to a post bake on a hot plate at a temperature of 230° C. for 30 minutes or at 300° C. for 30 minutes and, in the same manner as described above, the transmittance of each coating film at a wavelength of 400 nm was measured. The result of the measurement is shown in Table 3.

The measurement result of a UV-vis spectrum (200-800 nm) of a coating film (post bake: at 300° C. for 30 minutes) obtained using the polymer compound [5] of Example 2 is shown in FIG. 7 and the measurement result of a UV-vis spectrum (200 to 800 nm) of a coating film (post bake: at 300° C. for 30 minutes) obtained using the polymer compound [13] of Example 5 is shown in FIG. 8.

TABLE 3

| | After baking at 110° C. | After post bake at 230° C. | After post bake at 300° C. |
|---|---|---|---|
| Example 2 (compound [5]) | 96.5% | 95.4% | 96.1% |
| Example 5 (compound [13]) | 95.7% | 89.6% | 88.6% |

As shown in Table 3, there was obtained the result that the coating films prepared from the compounds obtained in Example 2 and Example 5 maintain advantageous transparency at 400 nm also after the post bake and combine heat resistance.

<Evaluation of Refractive Index>

The polymer compound [5] obtained in Example 2 was dissolved in DMAc and the polymer compound [13] obtained in Example 5 was dissolved in PGME to prepare each solution with a concentration of 5% by weight.

Each solution was applied on a silicon wafer using a spin coater and each resultant coating film was subjected to baking on a hot plate at a temperature of 110° C. for 120 seconds to form a coating film having a film thickness of 100 nm. The refractive index at 633 nm of each coating film was measured.

The refractive index of a coating film formed from the polymer compound [5] obtained in Example 2 and the refractive index of a coating film formed from the polymer compound [13] obtained in Example 5 were found to be 1.67 and 1.69, respectively.

<Birefringence Index of Polymer Compound>

A 12% by weight PGME solution of the polymer compound [13] obtained in Example 5 was prepared and the solution was spin-coated on a 3 cm×3 cm silicon substrate at 700 rpm for 20 seconds, followed by baking the solution at 110° C. for 5 minutes and at 150° C. for 10 minutes to obtain a homogeneous thin film having a film thickness of 1.2 µm. The birefringence index of the thin film was measured using a prism coupler and was found to be 0.002.

In the same manner as described above, a 8% by weight 1,2-dichlorobenzene solution of the linear polymer compound obtained in Comparative Example 1 was prepared and, according to the same procedure as described above, the solution was spin-coated on a silicon substrate. As the result, the spin-coated film became a thin film having a glaring unevenness. The birefringence index of the thin film was measured and was found to be 0.006.

In other words, there was obtained the result that the polymer compound [13] obtained in Example 5 has a birefringence index lower than that of the linear polymer of Comparative Example 1.

<Electron Microscope Observation of Polymer Compound>

A 0.5% by weight THF solution of each of the polymer compounds [5] and [13] obtained in Example 2 and Example 5, respectively, was prepared and each solution was dropped into a copper mesh grid and was subjected to observation under a transmission electron microscope.

The resultant microscope photographs are shown in FIG. 9 (Example 2: polymer compound [5]) and in FIG. 10 (Example 5: polymer compound [13]). According to these photographs, there were observed a particle-shaped structure having a diameter of 10-100 nm in FIG. 9 (Example 2) and a particle-shaped structure having a diameter of 2-10 nm in FIG. 10 (Example 5).

On the other hand, with respect to the linear polymer obtained in Comparative Example 1, in the same manner as described above, the observation under a transmission electron microscope was performed. However, no structure could be observed.

Preparation of Thermocurable Film Forming Polymer Composition: Example 10 to Example 12 and Comparative Example 2

Each of the compositions of Example 10 to Example 12 and Comparative Example 2 was prepared according to the formulations shown in Table 4. Each composition was subjected to the evaluation of refractive index, solvent resistance, transmittance, heat resistance, and viscosity.

As the component (A), there were used the polymer compound [13] obtained in Example 5 and the polymer compound [24] obtained in Comparative Example 1.

Here, [24] used in Comparative Example 2 was not dissolved in PGME, so that NMP was used as the solvent in Comparative Example 2.

TABLE 4

|  | Component (A) (g) | Component (B) (g) | Solvent (g) |
|---|---|---|---|
| Example 10 | [13] 3.0 | GT4 0.6 | PGME 20.4 |
| Example 11 | [13] 3.0 | CEL 0.6 | PGME 20.4 |
| Example 12 | [13] 3.0 | BPAG 0.6 | PGME 20.4 |
| Comparative Example 2 | [24] 3.0 | GT4 0.6 | NMP 17.0 |

[Evaluation of Refractive Index]

Each of the compositions of Example 10 to Example 12 and Comparative Example 2 was applied on a silicon wafer using a spin coater and was pre-baked on a hot plate at a temperature of 100° C. for 120 seconds to form a coating film having a film thickness of 1.7 μm. The film thickness was measured using F20 (manufactured by Filmetrics Inc.). The coating film was post-baked on a hot plate at a temperature of 230° C. for 30 minutes to form a cured film having a film thickness of 1.5 μm. The refractive index of the coating film at 633 nm was measured by a multiple incident angle spectro ellipsometer (VASE; manufactured by J. A. Woollam Japan Co., Ltd.).

[Evaluation of Solvent Resistance]

Each of the compositions of Example 10 to Example 12 and Comparative Example 2 was applied on a silicon wafer using a spin coater and was pre-baked on a hot plate at a temperature of 100° C. for 120 seconds to form a coating film having a film thickness of 1.7 μm. The film thickness was measured using F20 (manufactured by Filmetrics Inc.). The coating film was post-baked on a hot plate at a temperature of 230° C. for 30 minutes to form a cured film having a film thickness of 1.5 μm.

The cured film was immersed in NMP for 60 seconds and was dried at a temperature of 100° C. for 60 seconds to measure the film thickness. A cured film in which a change in the film thickness was not observed after the immersion in NMP was evaluated as "A" and a cured film in which a decrease of the film thickness was observed after the immersion was evaluated as "C".

[Evaluation of Light Transmittance (Transparency)]

Each of the compositions of Example 10 to Example 12 and Comparative Example 2 was applied on a quartz substrate using a spin coater and was pre-baked on a hot plate at a temperature of 100° C. for 120 seconds to form a coating film having a film thickness of 1.7 μm. The film thickness was measured using F20 (manufactured by Filmetrics Inc.). The coating film was post-baked on a hot plate at a temperature of 230° C. for 30 minutes to form a cured film having a film thickness of 1.5 μm.

The transmittance of the cured film at a wavelength of 400 nm was measured using an ultraviolet-visible spectrophotometer (model number SHIMADZU UV-2550; manufactured by Shimadzu Corporation).

This cured film was further baked on a hot plate at 300° C. for 30 minutes and the transmittance of the baked cured film at a wavelength of 400 nm was measured using the ultraviolet-visible spectrophotometer.

[Evaluation of Viscosity]

The viscosity of each of the compositions of Example 10 to Example 12 and Comparative Example 2 was measured using an E type viscometer (VISCO METER TV20; manufactured by Toki Sangyo Co., Ltd.) at 25° C.

[Result of Evaluations]

The result of the above evaluations is shown in Table 5.

TABLE 5

|  | Refractive index | Solvent resistance | Transmittance[*1] ($\lambda$ = 400 nm) After post-bake | Transmittance[*1] ($\lambda$ = 400 nm) After further bake | Viscosity (mPa·s) |
|---|---|---|---|---|---|
| Example 10 | 1.67 | A | 92% | 92% | 12 |
| Example 11 | 1.67 | A | 92% | 92% | 12 |
| Example 12 | 1.68 | A | 91% | 91% | 12 |
| Comparative Example 2 | 1.68 | C | 90% | 89% | 25 |

[*1] Transmittance After post-bake: transmittance after post-bake at 230° C. (for 30 minutes)
After further bake: transmittance after further heating treatment at 300° C. (for 30 minutes) after post-bake at 230° C. (for 30 minutes)

Each of the cured films obtained from the compositions of Example 10 to Example 12 had a high refractive index and was regarded as having resistance against NMP. Each of them had a high transmittance (transparency) and could achieve a high transmittance even after heating at 300° C. Each composition had a low viscosity.

On the other hand, the cured film of Comparative Example 2 had glaring unevenness to be regarded as having no resistance against NMP.

As described above, when made into a solution, the thermocurable film forming polymer composition of the present invention has a low viscosity as well as excellent solvent resistance after thermal curing. The resultant cured film has a high refractive index and excellent light transmittance and the cured film after being subjected to a further high temperature treatment has advantageous light transmittance and excellent heat resistance.

INDUSTRIAL APPLICABILITY

The polymer compound of the present invention and a solution or a coating film containing the compound are applicable to a protective film for a liquid crystal display element, a TFT array planarizing film, an overcoat for a color filter and the like, a spacer material, a light-retrieve enhancing film of an EL display, a light-intake enhancing layer of an imaging element, a light-intake enhancing layer of an LED element, and the like.

The thermocurable film forming polymer composition according to the present invention is suitable as a material for forming a light-retrieving efficiency enhancing layer of an LED element or a solid imaging element and a cured film such as a protective film, a planarizing film, and an insulating film in various displays such as a thin film transistor (TFT) type liquid crystal display element and an organic EL element.

Figure 1:
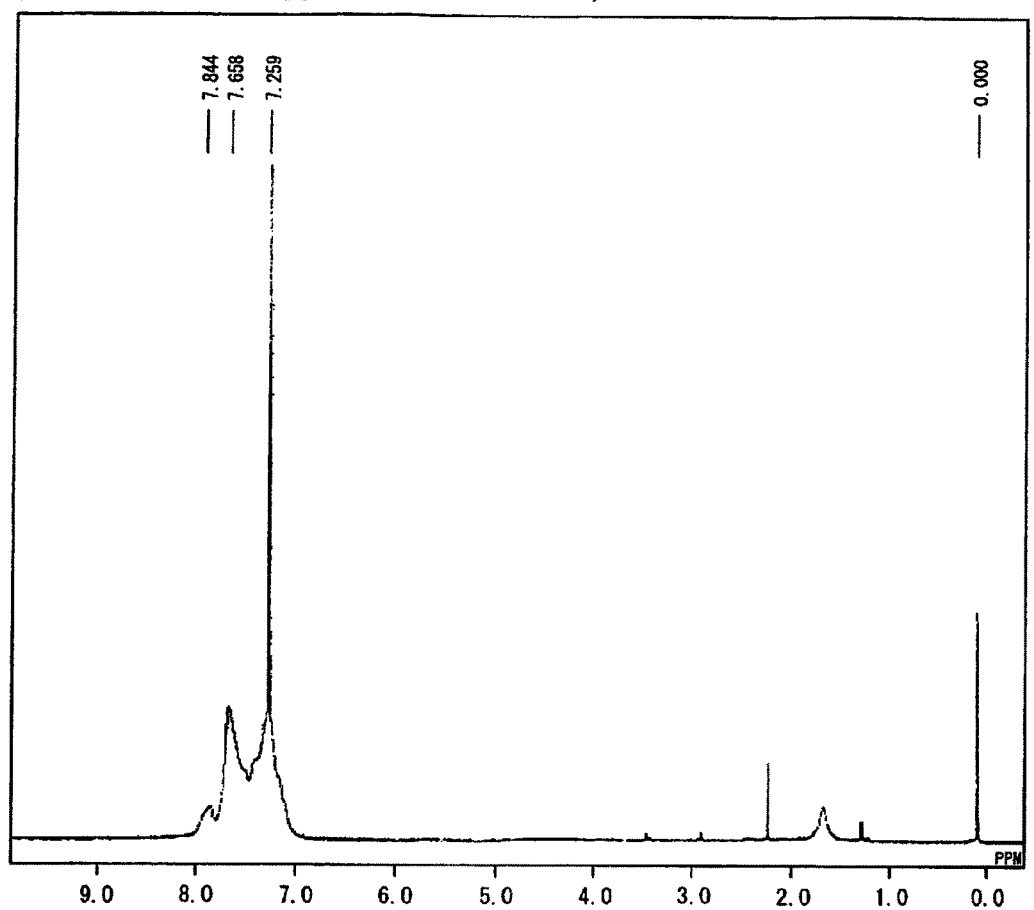
FIG. 1 is a diagram showing a measurement result of $^1$H NMR spectrum of the polymer compound [5] obtained in Example 2.
Figure 2:
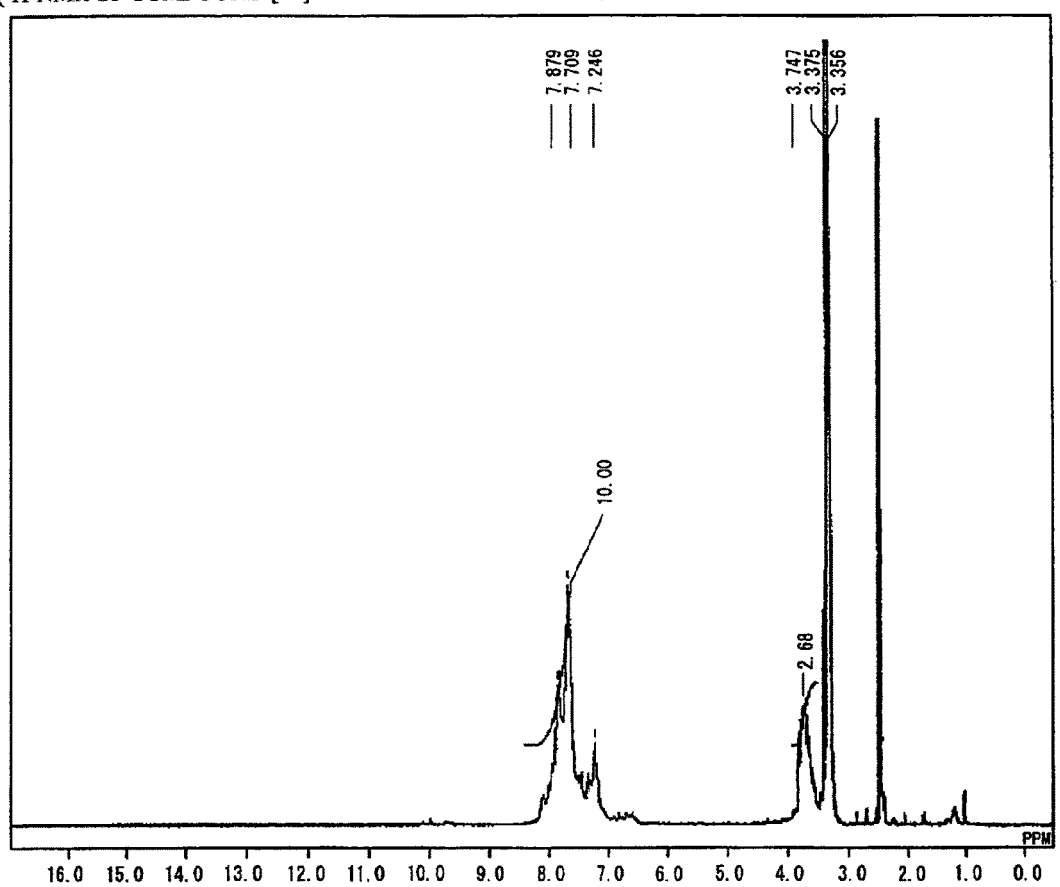
FIG. 2 is a diagram showing a measurement result of $^1$H NMR spectrum of the polymer compound [12] obtained in Example 4.
Figure 3:
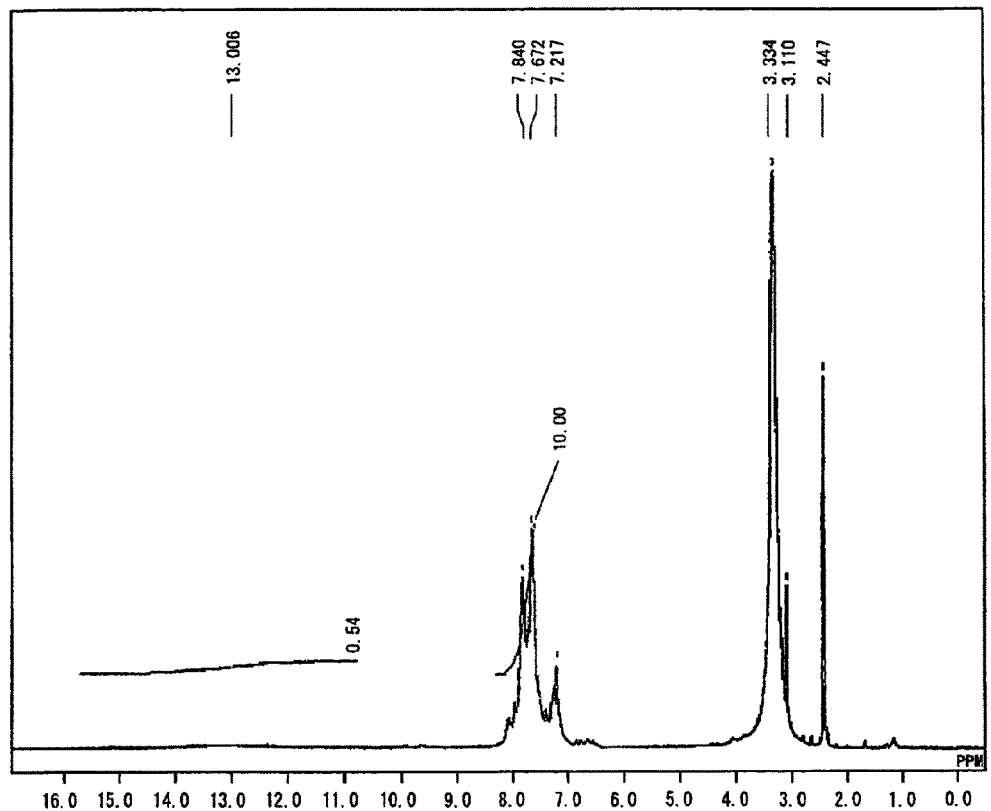
FIG. 3 is a diagram showing a measurement result of $^1$H NMR spectrum of the polymer compound [13] obtained in Example 5.
Figure 4:
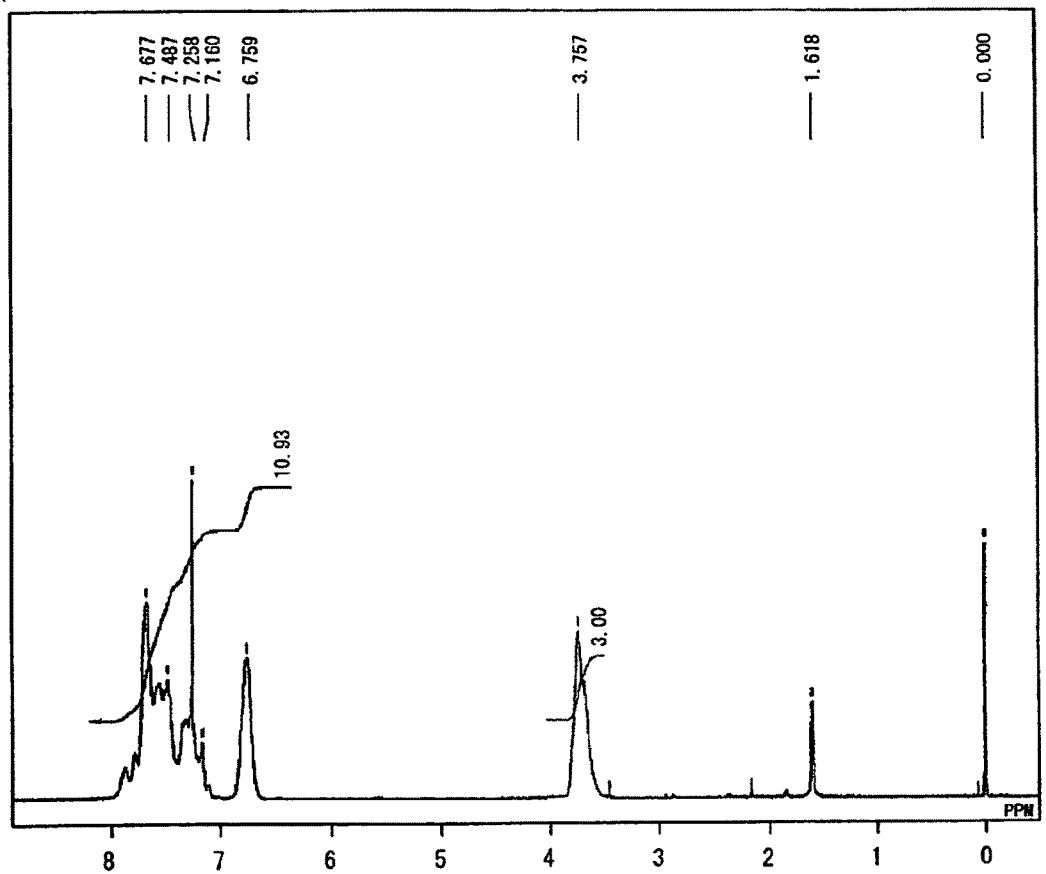
FIG. 4 is a diagram showing a measurement result of $^1$H NMR spectrum of the polymer compound [17] obtained in Example 7.
Figure 5:
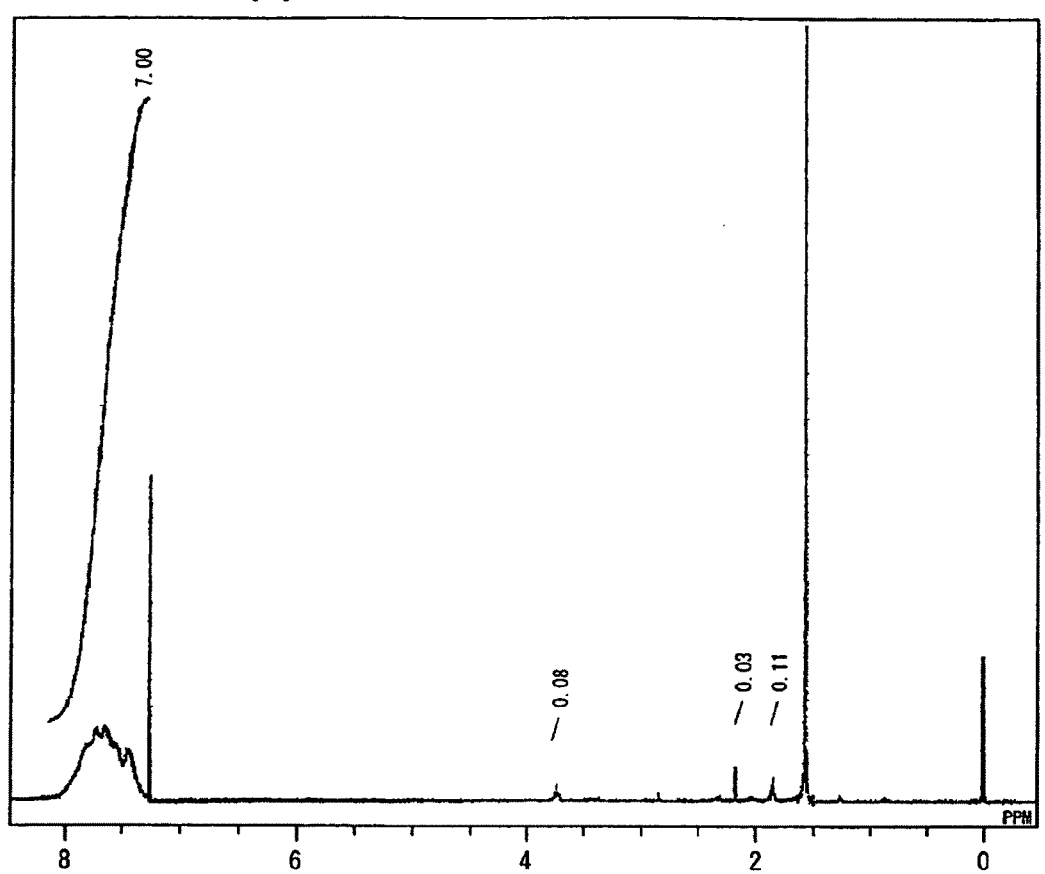
FIG. 5 is a diagram showing a measurement result of $^1$H NMR spectrum of the polymer compound [21] obtained in Example 9.
Figure 6:
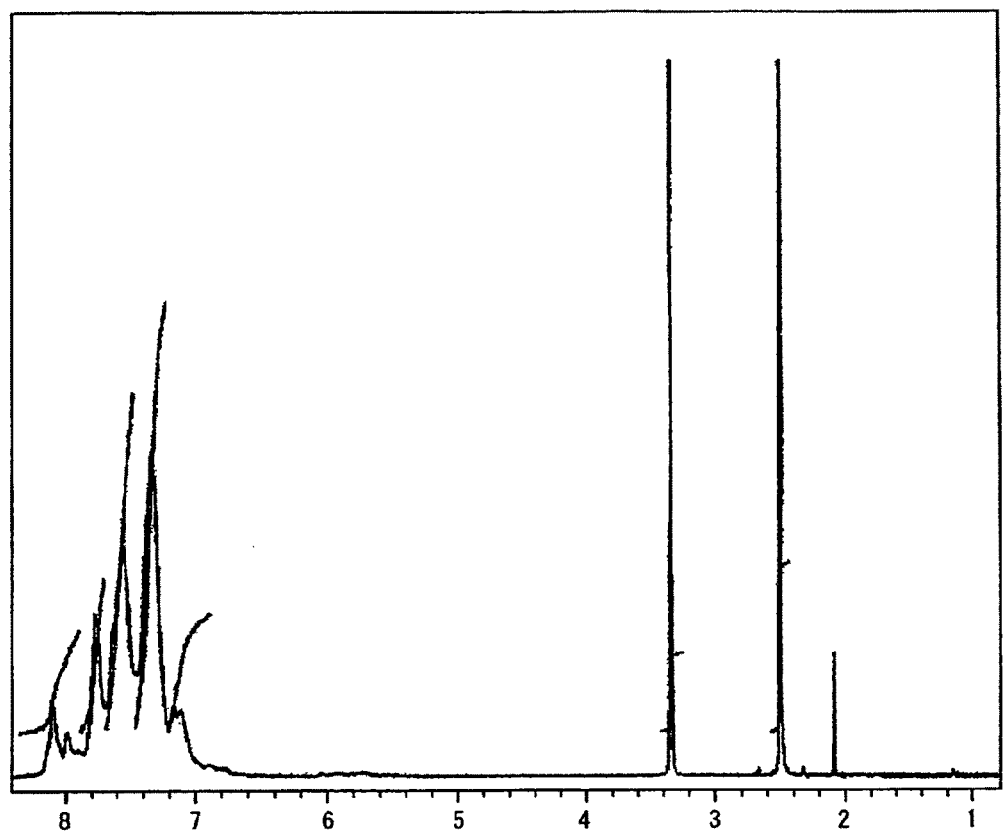
FIG. 6 is a diagram showing a measurement result of $^1$H NMR spectrum of the linear polymer compound obtained in Comparative Example 1.
Figure 7:
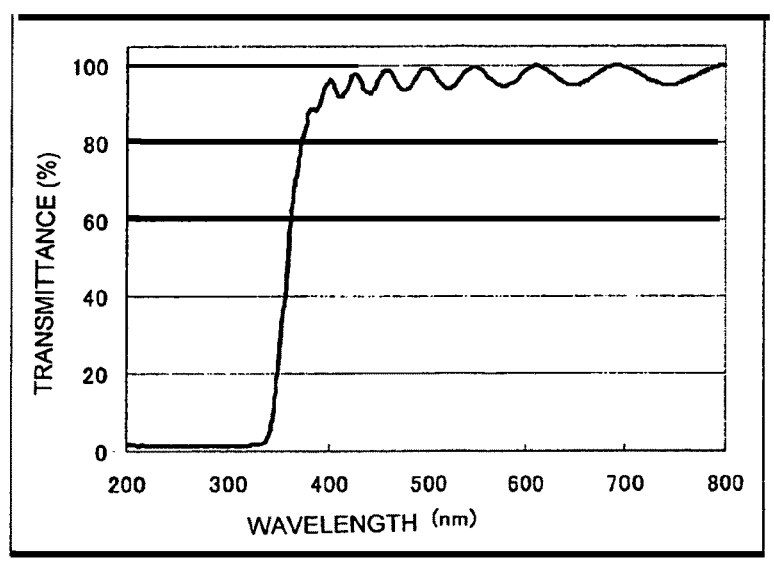
FIG. 7 is a diagram showing a measurement result of UV-Vis spectrum of the coating film (post bake: at 300° C. for 30 minutes) produced using the polymer compound [5] obtained in Example 2.
Figure 8:
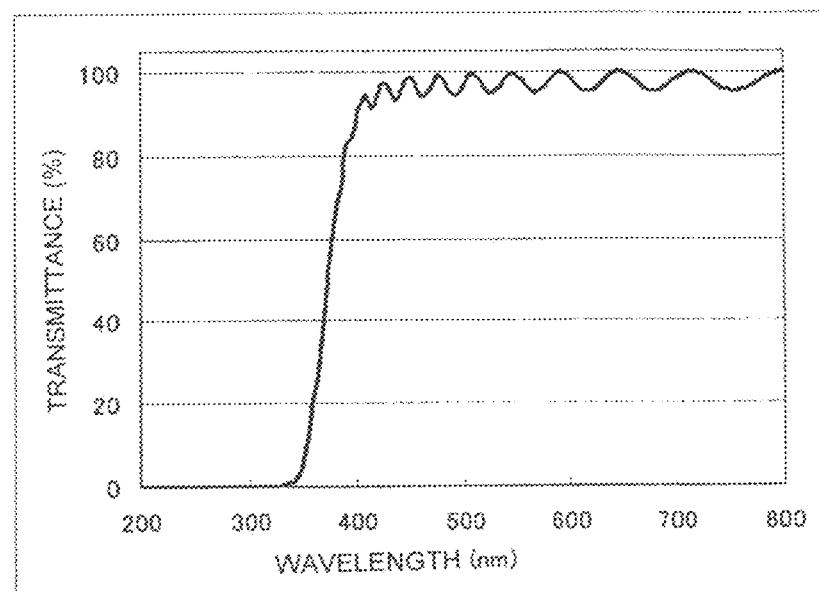
FIG. 8 is a diagram showing a measurement result of UV-Vis spectrum of the coating film (post bake: at 300° C. for 30 minutes) produced using the polymer compound [13] obtained in Example 5.
Figure 9:
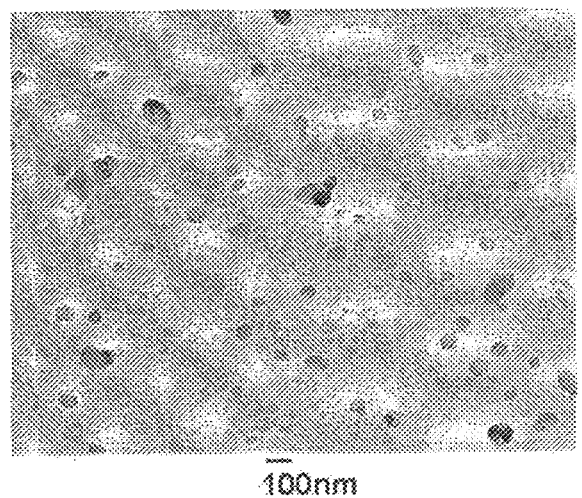
FIG. 9 is a photograph taken in the observation of a solution of the polymer compound [5] obtained in Example 2 under a transmission type electron microscope.
Figure 10:
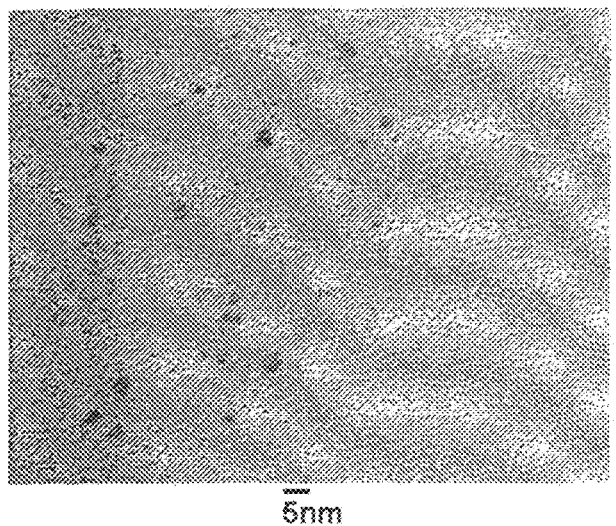
FIG. 10 is a photograph taken in the observation of a solution of the polymer compound [13] obtained in Example 5 under a transmission type electron microscope.

The invention claimed is:

1. A polymer compound comprising a structure unit of Formula (3):

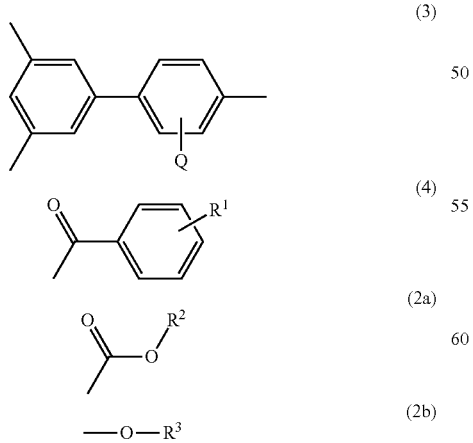

[in Formula (3), Q is a group of Formula (4); in Formula (4), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group].

2. The polymer compound according to claim 1, wherein in Formula (4), $R^1$ is a group of Formula (2a).

3. The polymer compound according to claim 1, wherein in Formula (4), $R^1$ is a group of Formula (2b).

4. A solution comprising the polymer compound as claimed in claim 1.

5. A coating film comprising the polymer compound as claimed in claim 1.

6. An aroylbiphenyl compound of Formula (1):

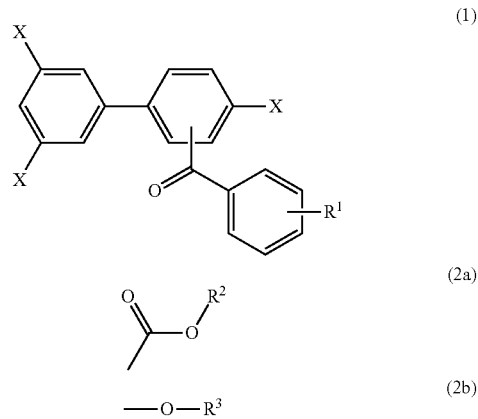

[in Formula (1), X is a halogen atom, and $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group].

7. A thermocurable film forming polymer composition comprising:

as a component (A), a polymer compound containing a structure unit of Formula (19):

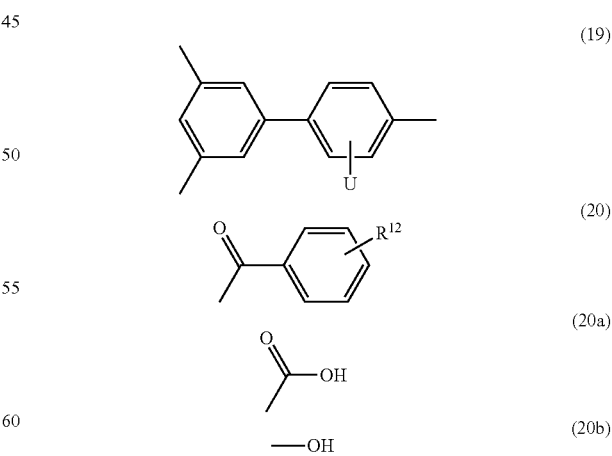

[in Formula (19), U is a group of Formula (20); and in Formula (20), $R^{12}$ is a group of Formula (20a) or Formula (20b)]; and as a component (B), a crosslinkable compound.

43

8. The thermocurable film forming polymer composition according to claim 7, wherein in Formula (20), $R^{12}$ is a group of Formula (20a).

9. The thermocurable film forming polymer composition according to claim 7, wherein the component (A) is a polymer compound consisting of a structure unit of Formula (19).

10. The thermocurable film forming polymer composition according to claim 7, wherein the component (B) is a crosslinkable compound having an epoxy group or a crosslinkable compound having an oxetanyl group.

11. The thermocurable film forming polymer composition according to claim 7, wherein the component (A) and the component (B) are in a solution state of being dissolved in an organic solvent.

12. A cured film obtained using the thermocurable film forming polymer composition as claimed in claim 7.

13. A solid imaging element comprising the cured film as claimed in claim 12.

14. An LED element comprising the cured film as claimed in claim 12.

15. A production method of a polymer compound comprising polymerizing a compound of Formula (18):

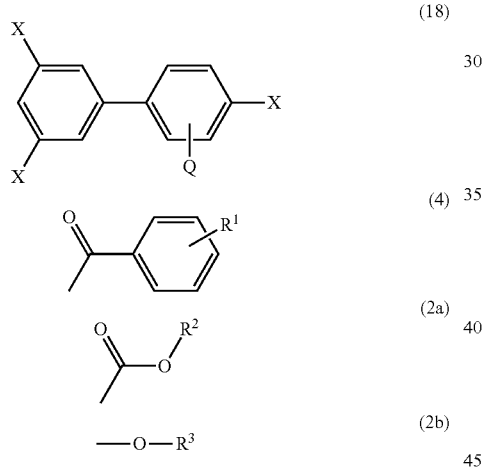

[where X is a halogen atom, and Q is a group of Formula (4); in Formula (4), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group]

in the presence of at least one of a nickel complex and a palladium complex.

16. A production method of the aroylbiphenyl compound as claimed in claim 6, comprising reacting a compound of Formula (5) with a compound of Formula (6):

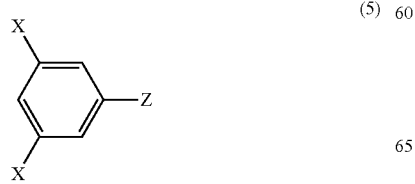

44

-continued

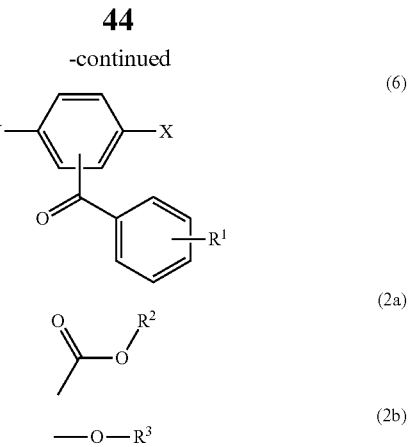

[in Formula (5) and Formula (6), X is a halogen atom, and Z and Y are a group selected from a group A below or a group B below, when Z is a group selected from the group A, Y is a group selected from the group B, and when Z is a group selected from the group B, Y is a group selected from the group A; in Formula (6), $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group], Group A: $MgR^4$, Li, $Al(R^4)_2$, $ZnR^4$, $Sn(R^5)_3$, $B(OR^6)_2$, $Si(R^5)_3$ (in these formulae, $R^4$ is a halogen atom or a $C_{1-6}$ alkoxy group, $R^5$ is a halogen atom, a $C_{1-6}$ alkyl group, or a $C_{1-6}$ alkoxy group, $R^6$ is a hydrogen atom or a $C_{1-6}$ alkyl group), Group B: a halogen atom, $R^7SO_3$ ($R^7$ is a $C_{1-10}$ alkyl group, a $C_{1-10}$ alkyl group substituted with a fluorine atom, or a benzene ring (which is optionally substituted with an alkyl group))

in the presence of a transition metal catalyst.

17. A production method of the aroylbiphenyl compound as claimed in claim 6, comprising:

reacting a compound of Formula (7) with an aromatic metal compound of Formula (8):

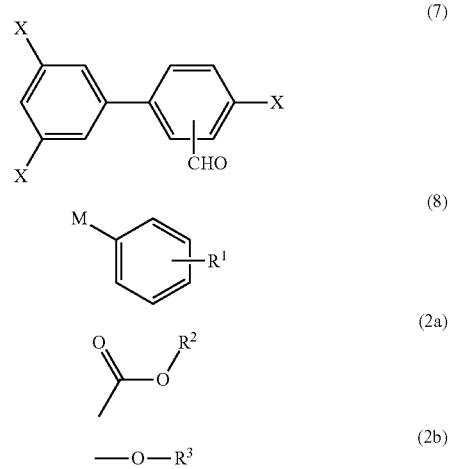

[in Formula (7), X is a halogen atom; in Formula (8), M is $MgR^4$, Li, $Al(R^4)_2$, $ZnR^4$, $Ti(R^4)_3$, or $Zr(R^4)_3$ (in these formulae, $R^4$ is a halogen atom or a $C_{1-6}$ alkoxy group), and $R^1$ is a hydrogen atom or a group of Formula (2a) or Formula (2b); and in Formula (2a) and Formula (2b), $R^2$ and $R^3$ are independently a hydrogen atom or a $C_{1-6}$ alkyl group]; and oxidizing a hydroxy group.

* * * * *